(12) United States Patent
Vinluan

(10) Patent No.: US 9,144,486 B2
(45) Date of Patent: Sep. 29, 2015

(54) FENESTRATED INFLATABLE GRAFT

(71) Applicant: TRIVASCULAR, INC., Santa Rosa, CA (US)

(72) Inventor: Jenine S. Vinluan, Petaluma, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 286 days.

(21) Appl. No.: 13/652,471

(22) Filed: Oct. 15, 2012

(65) Prior Publication Data

US 2013/0103135 A1 Apr. 25, 2013

Related U.S. Application Data

(60) Provisional application No. 61/547,421, filed on Oct. 14, 2011.

(51) Int. Cl.
*A61F 2/07* (2013.01)
*A61F 2/856* (2013.01)
*A61F 2/06* (2013.01)
*A61F 2/89* (2013.01)

(52) U.S. Cl.
CPC ... *A61F 2/06* (2013.01); *A61F 2/07* (2013.01); *A61F 2/89* (2013.01); *A61F 2002/061* (2013.01); *A61F 2002/065* (2013.01); *A61F 2002/067* (2013.01); *A61F 2002/072* (2013.01); *A61F 2220/0058* (2013.01); *A61F 2220/0075* (2013.01); *A61F 2250/0003* (2013.01); *A61F 2250/006* (2013.01); *A61F 2250/0069* (2013.01)

(58) Field of Classification Search
CPC ............ A61F 2/06; A61F 2/07; A61F 2/856; A61F 2250/0003; A61F 2250/0069
USPC ...................................... 623/1.13, 1.25, 1.35
See application file for complete search history.

(56) References Cited

U.S. PATENT DOCUMENTS

| 7,147,661 | B2 * | 12/2006 | Chobotov et al. | 623/1.16 |
| 7,413,573 | B2 * | 8/2008 | Hartley et al. | 623/1.13 |
| 2003/0093145 | A1 * | 5/2003 | Lawrence-Brown et al. | 623/1.21 |
| 2007/0055356 | A1 * | 3/2007 | Eidenschink | 623/1.25 |
| 2010/0280598 | A1 * | 11/2010 | Fox | 623/1.32 |

* cited by examiner

*Primary Examiner* — Kathleen Holwerda
(74) *Attorney, Agent, or Firm* — Hoffmann & Baron, LLP

(57) ABSTRACT

The endovascular graft includes a tubular structure having a first end and a second end. The tubular structure has a wall which defines a lumen between the first and second ends. A fenestration is located between the first and second ends to extend through the wall of the tubular structure. A sealing ring is circumferentially disposed within or on, including without limitation secured to, the tubular structure. The sealing ring is adjacent to the fenestration. The sealing ring may be inflatable.

20 Claims, 14 Drawing Sheets

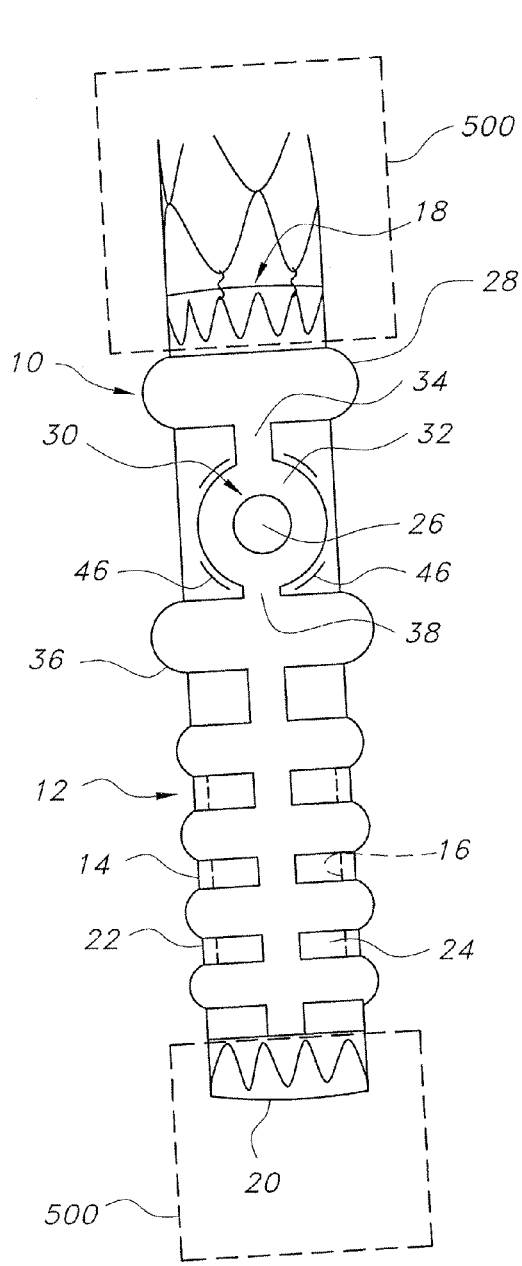
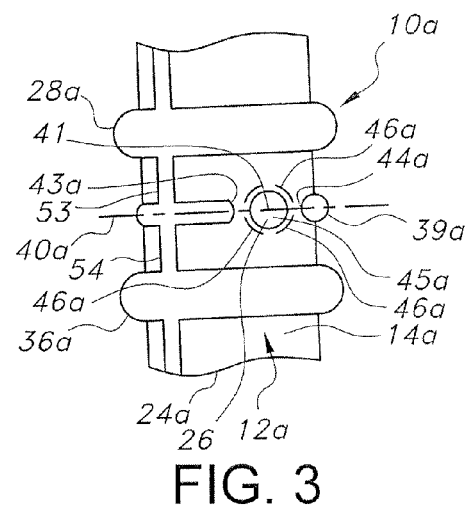
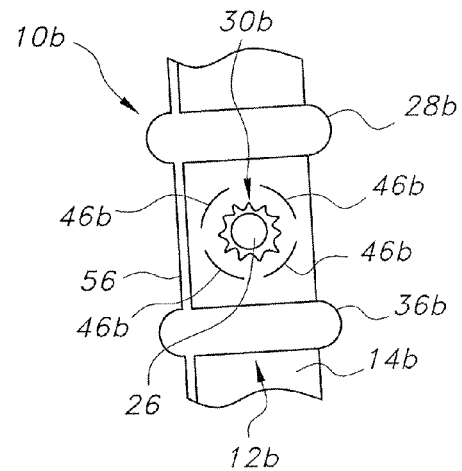
FIG. 2
FIG. 3
FIG. 4

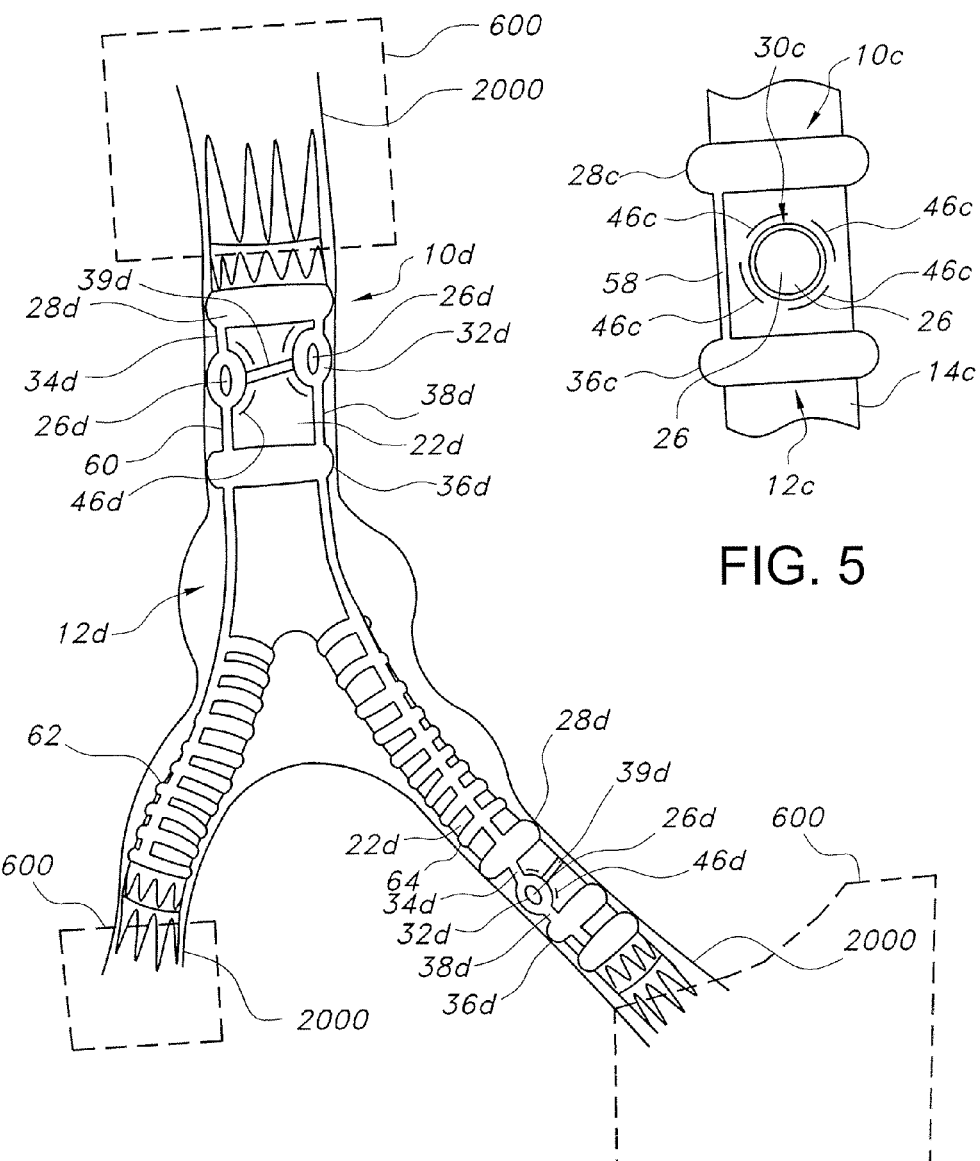

FENESTRATED INFLATABLE GRAFT

CROSS REFERENCE TO RELATED APPLICATION

This application claims the benefit of U.S. Provisional Application No. 61/547,421, filed Oct. 14, 2011, the entire contents of which are incorporated by reference herein.

FIELD OF THE INVENTION

The present invention relates generally to an endovascular graft or section thereof having a sealing ring and, more specifically, to an endovascular graft or section thereof having a fenestration and a sealing ring adjacent thereto.

BACKGROUND OF THE INVENTION

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aneurysms can have relatively high morbidity and mortality rates due to the risk factors inherent to surgical repair of this disease, as well as long hospital stays and painful recoveries. Due to the inherent risks and complexities of surgical repair of aortic aneurysms, endovascular repair has become a widely used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the Endurant® stent graft system manufactured by Medtronic, Inc. of Minneapolis, Minn., the Zenith® stent graft system sold by Cook, Inc. of Bloomington, Ind., the PowerLink® stent graft system manufactured by Endologix, Inc. of Irvine, Calif., and the Excluder® stent graft system manufactured by W.L. Gore & Associates, Inc. of Newark, Del. A commercially available stent graft for the treatment of TAAs is the TAG™ system manufactured by W.L. Gore & Associates, Inc.

Aneurysms and the like in the vasculature are a condition manifested by expansion and weakening of the walls of one or more vessels of the vasculature. Such conditions require intervention due to the severity of the sequelae. Methods of treating aneurysms have included invasive surgical methods with placement of a vascular graft within a vessel as a reinforcing member thereof. However, such a procedure requires a surgical cut of the vessel for access thereto which, in turn, can result in a rupture of the aneurysm due to the decreased external pressure from the organs and tissues surrounding the vessel, which are moved during the procedure to gain access thereto. Accordingly, surgical procedures have disadvantages due to the possibility of the rupture of the aneurysm in addition to other factors. Such other factors can include a declined physical condition of the patient due to blood loss, anuria, and low blood pressure associated with the aneurysm.

Aneurysms may occur in a section of the vessel near a central section thereof from which one or more branch vessels extend. A vascular graft that is deployed in a section of the vessel near the central section preferably accommodates such one or more branch vessels by providing for the flow of blood that is within the graft into the branch vessels as would occur in the absence of the graft. Also, the vascular graft preferably provides for the flow of blood that is within the branch vessels into the central section also as would occur in the absence of the graft.

An aneurysm located near one or more branch vessels may result in a graft landing zone in the aneurysm's central section that has a relatively short axial length for supporting the vascular graft. Consequently, providing a seal between the vascular graft and central section in this landing zone may be difficult. Such a seal is advantageous to obstruct the flow of blood from the branch vessels through an annular clearance which may be present between the vascular graft and central section to the aneurysm. Preventing the flow of blood into the aneurysm is advantageous since the aneurysm is a weakened section of the wall of the vessel and, consequently, normally has limited capability to contain blood therein.

SUMMARY OF THE INVENTION

The present invention relates to a system and method for the treatment of disorders of the vasculature, particularly aneurysms. More specifically, the present invention relates to a system and method for treatment of aneurysms and the like in the vasculature which is a condition manifested by expansion and weakening of the walls of one or more vessels of the vasculature.

The endovascular graft of the present invention includes a tubular structure having a first end and a second end. The tubular structure has a wall which defines a lumen between the first and second ends. A fenestration is located between the first and second ends to extend through the wall of the tubular structure. A sealing ring is circumferentially disposed within or on, including without limitation secured to the tubular structure. The sealing ring is adjacent to the fenestration. The sealing ring may be inflatable.

The fenestration provides an opening through which blood, which is within the tubular structure, may exit therefrom and flow into one or more branch vessels which extend from the central section of the vessel of the vasculature. Also, the fenestration provides an opening through which blood, which is within the branch vessels, may flow into the tubular structure.

The sealing ring provides a seal between the tubular structure and the inner surface of the vessel of the vasculature. This seal obstructs the flow of blood through an annular clearance which may be present between the tubular structure and inner surface of the vessel. Blood which enters this annular clearance bypasses the interior of the tubular structure and may flow into an aneurysm in the vessel. Consequently, preventing the flow of blood into this annular clearance is advantageous.

In some embodiments, there is provided an endovascular graft including (i) a tubular structure having a first end and a second end and an outer surface and an inner surface; (ii) a sealing ring disposed on the outer surface of the tubular structure; and (iii) an attachment member, wherein the attachment member is positioned adjacent to the sealing ring.

In another embodiment, there is provided an endovascular graft including (i) a tubular structure having a first end and a second end and an outer surface and an inner surface; (ii) a seal ring deposited on the outer surface of the tubular structure; (iii) one or more branch portions emanating from the tubular structure; (iv) an inflation ring deposited on the outer surface of the branch portions; and (v) an attachment member, wherein the attachment member is positioned adjacent to the seal ring.

In some embodiments, a graft of the present invention desirably includes a lateral fenestration with seal rings. In some embodiments, a graft of the present invention desirably includes a lateral branch portion. In some embodiments, a graft of the present invention desirably includes a seal ring/ support ring. In some embodiments, a graft of the present invention is desirably self-expanding with the use of nitinol or balloon expandable with stainless steel, cobolt, chromium and the like. In some embodiments, a graft of the invention is desirably wire wound.

These and other features of the invention will be more fully understood from the following description of specific embodiments of the invention taken together with the accompanying drawings.

BRIEF DESCRIPTION OF THE DRAWINGS

In the drawings:

FIG. 2 is an elevational view of the endovascular graft of FIG. 1, the endovascular graft being shown as having a substantially straight configuration with a lateral sealing ring and fenestration.

FIG. 3 is an elevational view in schematic of a section of an embodiment of the endovascular graft of FIG. 2, the endovascular graft being shown as having an intermediate sealing ring the ends of which are closed.

FIG. 4 is an elevational view in schematic of a section of an embodiment of the endovascular graft of FIG. 2, the endovascular graft being shown as having a lateral support member which includes a metal structure.

FIG. 5 is an elevational view in schematic of a section of an embodiment of the endovascular graft of FIG. 2, the endovascular graft being shown as having a lateral support member which includes a bead structure; and FIG. 6 is an elevational view in schematic of an embodiment of the endovascular graft of FIG. 1, the endovascular graft being shown as being bifurcated.

DETAILED DESCRIPTION OF THE INVENTION

Embodiments of the invention are directed generally to methods and devices for treatment of fluid flow vessels with the body of a patient. Treatment of blood vessels is specifically indicated for some embodiments, and, more specifically, treatment of aneurysms, such as abdominal aortic aneurysms. With regard to graft embodiments discussed herein and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 1:
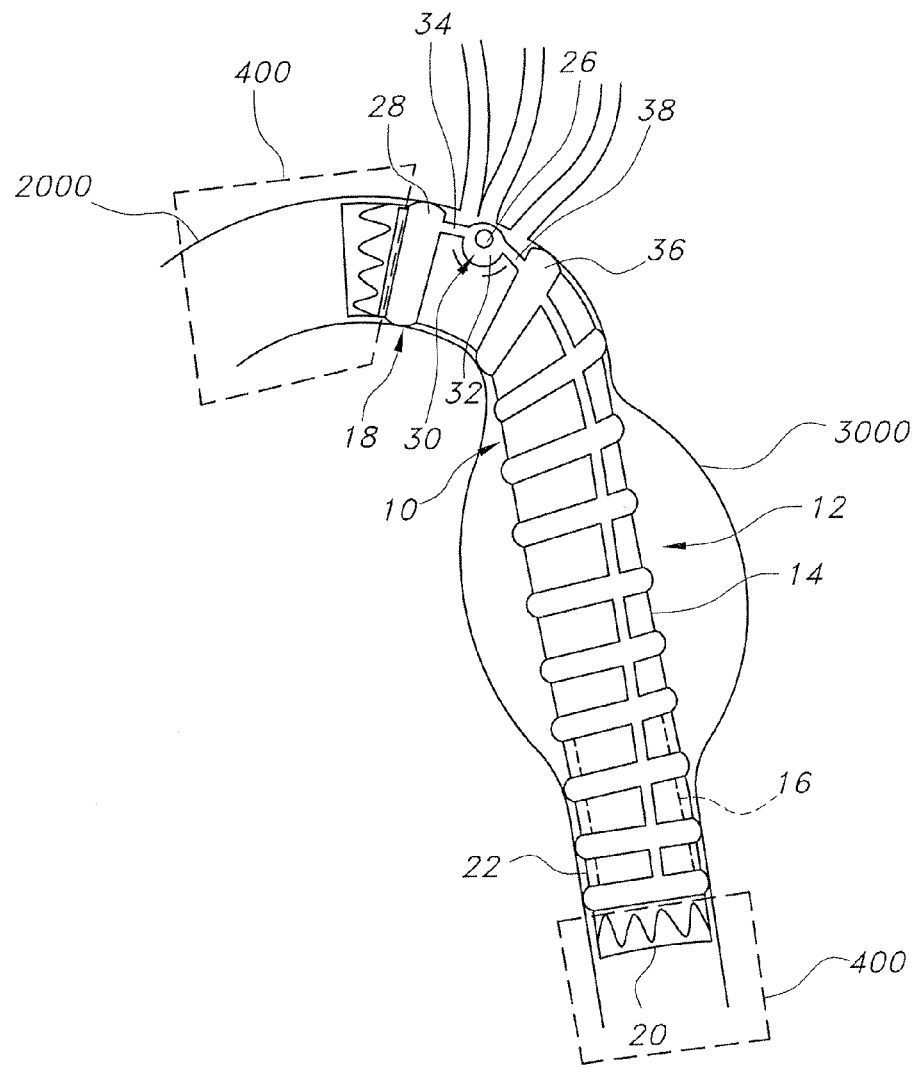
FIG. 1 is an elevational view in schematic of an endovascular graft in accordance with the present invention, the endovascular graft being shown within a vessel and the front half of the vessel being shown as removed.

Referring to the drawings and more specifically to FIG. 1 and FIG. 2, the endovascular graft 10 includes a tubular structure 12 having an outer surface 14 and an inner surface 16. The tubular structure 12 has a first end 18 and a second end 20. The tubular structure 12 has a wall 22 which defines a lumen 24 between the first and second ends 18, 20. The endovascular graft 10 includes a fenestration 26 which is located between the first end 18 and the second end 20. The fenestration 26 extends through the wall 22 of the tubular structure 12.

A sealing ring, which defines a proximal sealing ring 28, is circumferentially disposed within or on, including without limitation to the tubular structure 12. The proximal sealing ring 28 is located adjacent to and upstream of the fenestration 26. The proximal sealing ring 28 is inflatable.

The endovascular graft 10 includes a sealing ring, which defines a distal sealing ring 36, that is circumferentially disposed within or on, including without limitation secured to, the tubular structure 12. The distal sealing ring 36 is adjacent to and downstream of the fenestration 26. The distal sealing ring 36 is inflatable.

The endovascular graft 10 includes a lateral support member 30 that is disposed within or on, including without limitation secured to the tubular structure 12 in coaxial relation to the fenestration 26 such that the fenestration is encircled by the lateral support member. The lateral support member 30 is defined by an inflatable lateral sealing ring 32. An axial channel 34 is disposed within or on, including without limitation secured to the outer surface 14 of the tubular structure 12. The axial channel 34 is located between and connected to the proximal sealing ring 28 and lateral sealing ring 32. The channel 34 provides communication between the proximal sealing ring 28 and lateral sealing ring 32 such that inflation of one of the proximal and lateral sealing rings provides inflation of the other of the proximal and lateral sealing rings. An axial channel 38 is disposed within or on, including without limitation, secured to the outer surface 14 of the tubular structure 12 such that the channel 38 is located between and connected to the lateral and distal sealing rings 32, 36. The channel 38 provides communication between the lateral and distal sealing rings 32, 36 such that inflation of one of the lateral and distal sealing rings provides inflation of the other of the lateral and distal sealing rings. The lateral sealing ring 32, when inflated, supports the fenestration 26 in an open configuration.

The endovascular graft 10 includes an arcuate intermediate sealing ring 39 that is circumferentially disposed within or on, including without limitation secured to, the outer surface 14 of the tubular structure 12. The intermediate sealing ring 39 has a longitudinal plane 40 which has an axial position relative to the tubular structure 12. The axial position of the longitudinal plane 40 is substantially the same as the axial position of the center 41 of the fenestration 26 relative to the tubular structure 12.

The intermediate sealing ring 39 has a first end 43 and a second end 44. The intermediate sealing ring 39 has a circumferential gap 45 between the first and second ends 43, 44. The intermediate sealing ring 39 is circumferentially positioned relative to the fenestration 26 such that the fenestration is within the gap 45.

The intermediate sealing ring 39 is inflatable. The first and second ends 43, 44 of the intermediate sealing ring 39 are connected to the lateral sealing ring 32. This connection provides for communication between the lateral and intermediate sealing rings 32, 39 such that inflation of one of the lateral and intermediate sealing rings provides inflation of the other of the lateral and intermediate sealing rings. The intermediate sealing ring 39, when inflated, supports the tubular structure 12 and lumen 24 in an open configuration.

An embodiment of the endovascular graft 10 does not include an intermediate sealing ring 39. In such an embodiment, the lateral sealing ring 32 includes a pair of semicircular sections which together encircle the fenestration 26.

The endovascular graft 10 includes radio-opaque markers 46 disposed within or on, including without limitation secured to the tubular structure 12 adjacent to the fenestration 26. The radio-opaque markers 46 are elongate and arcuate, and are adjacent to the outer periphery of the lateral sealing ring 32. The radio-opaque markers 46 generally are equidistant from one another and do not intersect the channels 34, 38 or the intermediate sealing ring 39.

The first end 18 of the endovascular graft 10 is defined by a transverse edge 47. The tubular structure 12 has an axial flap structure 48 with a transverse edge 47. The tubular structure 12 has a scalloped portion 49 which opens from the transverse edge 47. The scalloped portion 49 is contained within the flap structure 48.

The flap structure 48 has an inner surface to which a stent structure 50 is connected. The stent structure 50 has a first end 51 and a second end 52. The stent structure 50 is positioned axially relative to the tubular structure 12 such that the transverse edge 47 is between the first and second ends 51, 52.

The portion of the tubular structure 12 which is contiguous with the second end 20 has an axial flap structure and scalloped portion which corresponds to the flap structure 48 and scalloped portion 49. Connected to the portion of the tubular structure 12 which is contiguous with second end 20 is a stent structure which corresponds to the stent structure 50.

Another embodiment of endovascular graft 10a is shown in FIG. 3. Elements illustrated in FIG. 3 which correspond to elements illustrated in FIGS. 1 and 2 have, in FIG. 3, the same reference numeral as in FIGS. 1 and 2 with the addition of the suffix "a". In this embodiment, the endovascular graft 10a includes an intermediate sealing ring 39a, the first and second ends 43a, 44a of which are closed. The intermediate sealing ring 39a is circumferentially positioned relative to the fenestration 26 such that the fenestration is within the circumferential gap 45a.

The endovascular graft 10a includes an axial channel 53 which is disposed within or on, including without limitation secured to, the outer surface 14a of the tubular structure 12a. The axial channel 53 is located between and connected to the proximal sealing ring 28a and intermediate sealing ring 39a. The channel 53 provides communication between the proximal sealing ring 28a and intermediate sealing ring 39a such that inflation of one of the proximal and intermediate sealing rings provides inflation of the other of the proximal and intermediate sealing rings. The intermediate sealing ring 39a, when inflated, supports the tubular structure 12a and lumen 24a in an open configuration.

The endovascular graft 10a includes an axial channel 54 which is disposed within or on, including without limitation secured to, the outer surface 14a of the tubular structure 12a. The channel 54 is located between and connected to the distal sealing ring 36a and intermediate sealing ring 39a. The channel 54 provides communication between the distal sealing ring 36a and intermediate sealing ring 39a such that inflation of one of the distal and intermediate sealing rings provides inflation of the other of the distal and intermediate sealing rings.

An embodiment of the endovascular graft 10b is shown in FIG. 4. Elements illustrated in FIG. 4 which correspond to elements illustrated in FIGS. 1 and 2 have, in FIG. 4, the same reference numeral as in FIGS. 1 and 2 with the addition of the suffix "b". In this embodiment, the endovascular graft 10b includes an axial channel 56 which is disposed within or on, including without limitation secured to, the outer surface 14b of the tubular structure 12b. The channel 56 is located between and connected to the proximal sealing ring 28b and distal sealing ring 36b. The channel 56 provides communication between the proximal sealing ring 28b and distal sealing ring 36b such that inflation of one of the proximal and distal sealing rings provides inflation of the other of the proximal and distal sealing rings.

The lateral support member 30b is a metal structure which includes NiTi material. Other materials may be included in the metal structure of the lateral support member 30b in other embodiments thereof. The lateral support member 30b supports the fenestration 26 in an open configuration.

Another embodiment of endovascular graft 10c is shown in FIG. 5. Elements illustrated in FIG. 5 which correspond to elements illustrated in FIGS. 1 and 2 have, in FIG. 5, the same reference numeral as in FIGS. 1 and 2 with the addition of the suffix "c". In this embodiment, the endovascular graft 10c includes an axial channel 58 which is disposed within or on, including without limitation secured to, the outer surface 14c of the tubular structure 12c. The channel 58 is located between and connected to the proximal sealing ring 28c and distal sealing ring 36c. The channel 58 provides communication between the proximal sealing ring 28c and distal sealing ring 36c such that inflation of one of the proximal and distal sealing rings provides inflation of the other of the proximal and distal sealing rings.

The lateral support member 30c includes a bead structure which is formed of non-expanded polytetrafluoroethylene (PTFE) material. In another embodiment of the lateral support member 30c, the bead structure may include silicone material.

Another embodiment of the endovascular graft 10d is shown in FIG. 6. Elements illustrated in FIG. 6 which correspond to elements illustrated in FIGS. 1 and 2 have, in FIG. 6, the same reference numeral as in FIGS. 1 and 2 with the addition of the suffix "d". In this embodiment, the endovascular graft 10d includes a tubular structure 12d which is bifurcated. Consequently, the tubular structure 12d includes a trunk portion 60 and a pair of leg portions 62, 64 which extend from the trunk portion.

The endovascular graft 10d includes a pair of fenestrations 26d which extend through the wall 22d of the trunk portion 60. The endovascular graft 10d has proximal and distal sealing rings 28d, 36d, lateral sealing rings 32d, channels 34d, 38d, and an intermediate sealing ring 39d which are associated with the fenestrations 26d in the trunk portion 60, as shown in FIG. 6.

The endovascular graft 10d includes a fenestration 26d which extends through the wall 22d of the leg portion 64. The endovascular graft 10d has proximal and distal sealing rings 28d, 36d, a lateral sealing ring 32d, channels 34d, 38d, and an intermediate sealing ring 39d which are associated with the fenestration 26d in the leg portion 64, as shown in FIG. 6.

An embodiment of the endovascular graft 10d is possible which does not include intermediate sealing rings 39d in the trunk portion 60 and leg portion 64. In such an embodiment, the lateral sealing rings 32d in the trunk portion 60 and leg portion 64 include respective pairs of semicircular sections which together encircle the corresponding fenestrations 26d.

Figure 7:
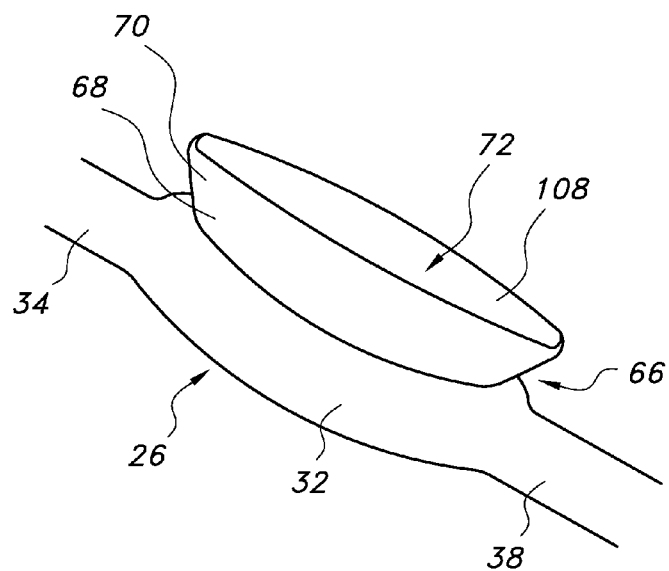
FIG. 7 is a perspective exploded view in schematic of the lateral sealing ring of the endovascular graft of FIG. 2 with an attachment member thereon.

In some embodiments, lateral sealing ring 32 may have an attachment member 66 positioned thereon, as shown in FIG. 7, which is a perspective exploded view in schematic of the lateral sealing ring 32 of the endovascular graft 10 of FIG. 2 with the lateral sealing ring 32 shown having an attachment member 66 thereon and with the axial channels 34 and 38 of the graft 10 partially shown. The attachment member 66 may be a separate element from lateral sealing ring 32 or may be integrally formed with lateral sealing ring 32. Desirably, attachment member 66 is sized to fit within a blood vessel.

Attachment member 66 may be any suitable attachment member known in the art. Suitable attachment members include, for example, tubular or substantially tubular structures, attachment rings, sinusoidal rings, eyelets, hooks, barbs, holes, snaps, "dog-bone" configurations, and combinations thereof.

In some embodiments, attachment member 66 may be a structure having a first end 68, a second end 70, an inside surface 108, and a lumen 72 disposed therein, as shown in FIG. 7. In such embodiments, the first end 68 of the attachment member 66 may be positioned on lateral sealing ring 32 in coaxial relationship thereto about fenestration 26 such that lumen 72 of attachment member 66 extends from fenestration 26 in continuous relationship thereto, as shown in FIG. 7.

Figure 8:
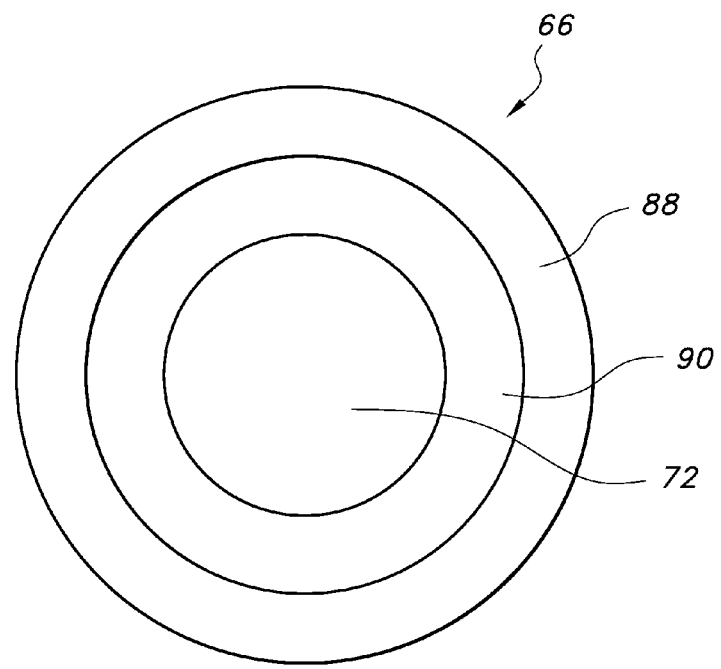
FIG. 8 is a top cross-sectional view of an attachment member having at least one outer layer of graft material and at least one inner layer of graft material.

Attachment member 66 may be made from any material desired, such as metals, polymers, and combinations thereof. Desirably, in some embodiments, attachment member 66 may be made from a polymeric material, such as expanded PTFE. In some embodiments, attachment member 66 may include at least one outer layer 88 and at least one inner layer 90 of supple layers of graft material, as shown in FIG. 8, which is a top cross-sectional view of attachment member 66 having at least one outer layer 88 of graft material and at least on inner layer 90 of graft material.

Figure 9:
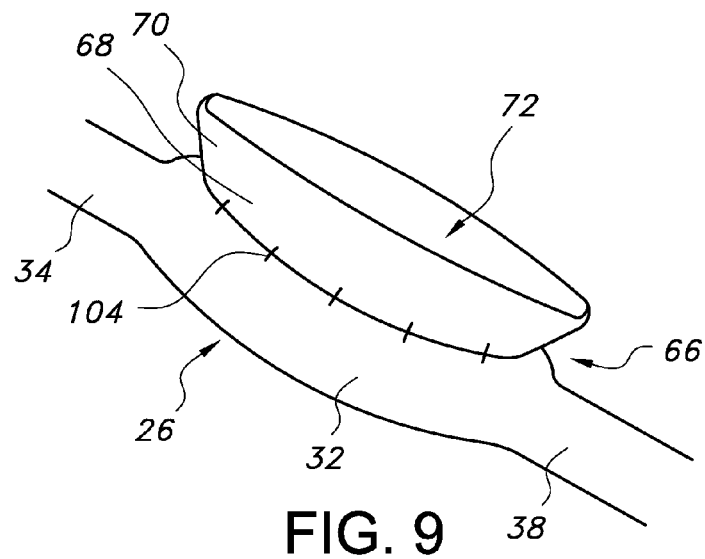
FIG. 9 is a perspective view in schematic of the attachment member of FIG. 7 shown disposed within or on, including without limitation secured to, the lateral sealing ring by a securing means.

In embodiments where attachment member 66 is a separate element, attachment member 66 may be attached to a lateral sealing ring 32 using any suitable securing means 104 known in the art, as shown in FIG. 9, which shows the attachment member 66 attached to a lateral sealing ring 32 by a securing means 104. Suitable securing means include, for example, attachment rings, sinusoidal rings, eyelets, hooks, barbs, holes, snaps, "dog-bone" configurations, and combinations thereof. Alternative securing means for securing attachment member 66 to a lateral sealing ring 32 include heat, compression, welding, sintering, suturing and combinations thereof.

Figure 10:
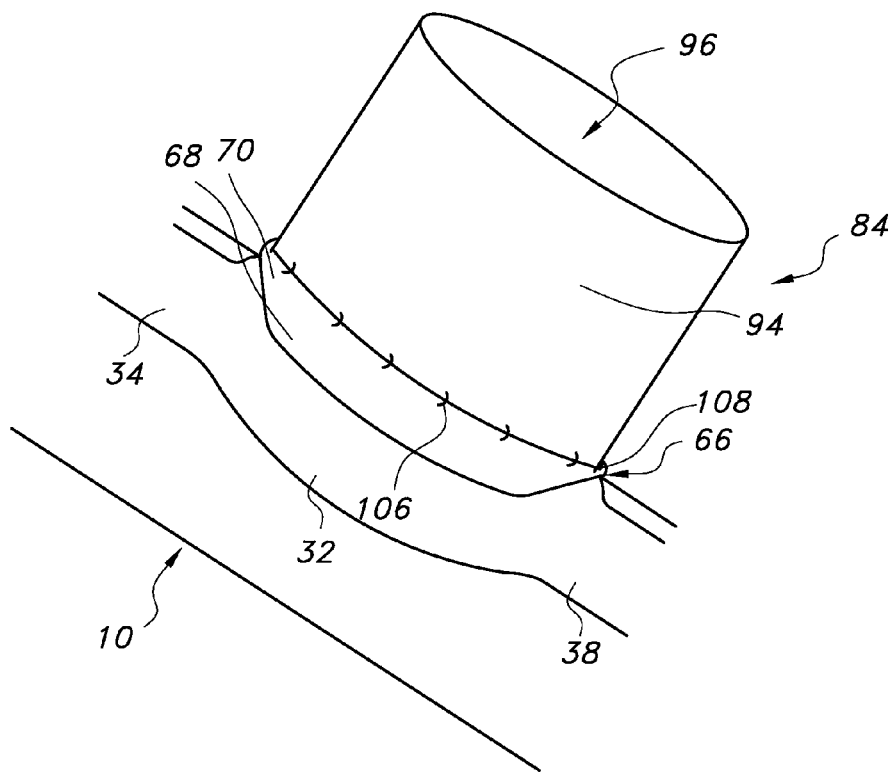
FIG. 10 is a perspective view in schematic of the lateral sealing ring of FIG. 7 shown positioned on the endovascular graft of FIG. 2 and with a graft extension attached thereto by means of the attachment member shown in FIG. 7.

Attachment member 66 may be used to attach a graft extension 84 to the endovascular graft 10, as shown in FIG. 10, which shows the attachment member 66 of FIG. 7 having a graft extension 84 secured thereto. As further shown in FIG. 10, graft extension 84 has a lumen 96 disposed therein. It will be understood that lumen 96 of graft extension 84 is in fluid communication with lumen 72 of attachment member 66. Desirably, a graft extension 84 is sized to fit within a blood vessel.

Attachment member 66 may be disposed within or on, including without limitation secured to, graft extension 84 using any suitable securing means 106 known in the art, as shown in FIG. 10. Suitable securing means include, for example, attachment rings, sinusoidal rings, eyelets, hooks, barbs, holes, snaps, "dog-bone" configurations, and combinations thereof. Alternative attachment means for securing the attachment member 66 to graft extension 84 include heat, compression, welding, sintering, suturing, and combinations thereof.

In some embodiments, graft extension 84 has an outer surface 94 which may be sized and configured to be sealed to an inside surface 108 of the attachment element 66 with the lumen 96 of graft extension 84 in fluid communication with lumen 72 of attachment element 66. Typically, an outer surface 94 of the graft extension 84 may be sealed to an inside surface 108 of the attachment element 66 when the endovascular graft 10 is in a deployed state.

For some embodiments, the axial length of the attachment member 66 may be sufficient to provide adequate surface area contact between an inside surface 108 of attachment element 66 and an outer surface 94 of graft extension 84. Additionally, the respective inside surface 108 of attachment element 66 should provide sufficient friction to the outer surface 94 of graft extension 84 to hold the graft extension 84 in place. Expandable members, such as expandable anchor members, sinusoidal rings and the like, may be used to expand the graft extension 84 against the inside surface 108 of the attachment member 66. Varying the amount of overlap between the attachment element 66 and the graft extension 84 can allow for different effective overall graft lengths to be achieved, thereby accommodating a range of anatomical sizes with fewer distinct main body and extension dimensions than would otherwise be required. For some embodiments, the attachment member 66 may have an axial length of at least about 1 cm. For some embodiments, the attachment member 66 may have an axial length of about 2 cm to about 6 cm, more specifically, about 3 cm to about 5 cm.

Figure 11:
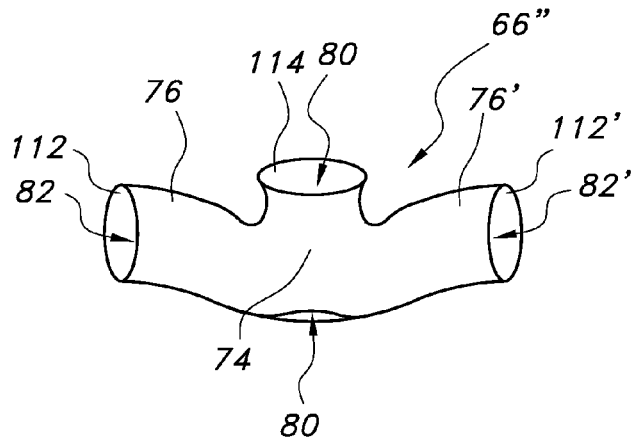
FIG. 11 is an elevational view in schematic of an attachment member having main and branch portions.

In some embodiments, an attachment member for use in the present invention may have a plurality of branch portions. As shown in FIG. 11, an attachment member 66" may have a main portion 74 and two or more branch portions 76, 76'. As shown in FIG. 11, main portion 74 may have an inner surface 114 and a lumen 80 disposed therein. Each branch portion 76, 76' may be a tubular or substantially tubular structure with a lumen 82, 82' disposed therein, as shown in FIG. 11. Each branch portion 76, 76' may be sized to fit within a blood vessel and has an inside surface 112, 112'. It will be understood that lumen 80 is in continuous relationship with lumens 82, 82' where branch portions 76, 76' extend from the main portion 74. Branch portions 76, 76' may be integrally formed with main portion 74 or may be separate elements from main portion 74. When branch portions 76, 76' are separate elements from main portion 74, they may be attached to main portion 74 using any suitable securing means known in the art including, for example, attachment rings, sinusoidal rings, eyelets, hooks, barbs, holes, snaps, "dog-bone" configurations, and combinations thereof. Alternative attachment means for securing the main portion 74 to branch portions 76, 76' include heat, compression, welding, sintering, suturing, and combinations thereof.

Figure 12:
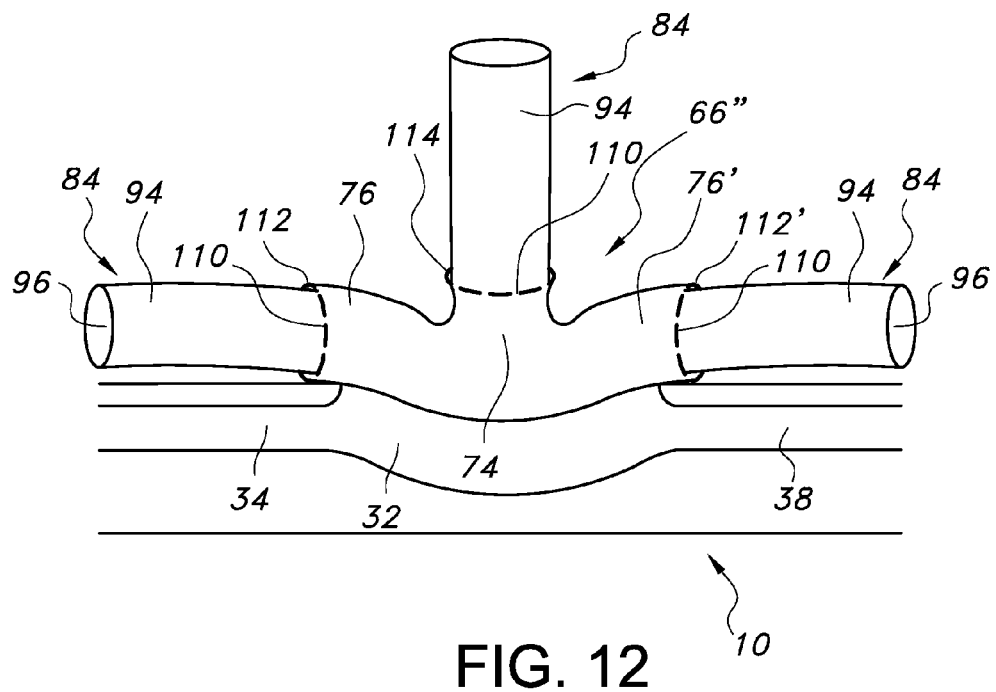
FIG. 12 is a perspective exploded view in schematic of the lateral sealing ring of the endovascular graft of FIG. 2 with the attachment member of FIG. 11 thereon.

In some embodiments, lateral sealing ring 32 may have an attachment member 66" positioned thereon, as shown in FIG. 12, which is a perspective exploded view in schematic of the endovascular graft 10 shown in FIG. 2 having an attachment member 66" positioned thereon. Attachment member 66" may be used to attach a graft extension 84 to the endovascular graft 10, as further shown in FIG. 12. Main portion 74 and each branch portion 76, 76' of attachment member 66" may be disposed within or on, including without limitation secured to, a graft extension 84 using any suitable securing means 110 known in the art. Suitable securing means 110 include, for example, attachment rings, sinusoidal rings, eyelets, hooks, barbs, holes, snaps, "dog-bone" configurations, and combinations thereof. Alternative attachment means for securing the attachment member 66" to a graft extension 84 include heat, compression, welding, sintering, and combinations thereof.

In some embodiments, a graft extension 84 has an outer surface 94 which may be sized and configured to be sealed to an inside surface 112 of branch portion 76 of attachment element 66". It will be understood that in such embodiments lumen 96 of a graft extension 84 is in fluid communication with lumen 82 of branch portion 76. Typically, an outer surface 94 of a graft extension 84 may be sealed to an inside surface 112 of the branch portion 76 of attachment element 66" when the endovascular graft 10 is in a deployed state.

In some embodiments, a graft extension 84 has an outer surface 94 which may be sized and configured to be sealed to an inside surface 112' of branch portion 76' of attachment element 66". It will be understood that, in such embodiments, lumen 96 of graft extension 84 is in fluid communication with lumen 82' of branch portion 76' of attachment element 66". Typically, an outer surface 94 of a graft extension 84 may be sealed to an inside surface 112' of the branch portion 76' of attachment element 66" when the endovascular graft 10 is in a deployed state.

In some embodiments, a graft extension 84 has an outer surface 94 which may be sized and configured to be sealed to an inside surface 114 of main portion 74 of attachment element 66". It will be understood that, in such embodiments, lumen 96 of graft extension 84 is in fluid communication with lumen 80 of main portion 74 of attachment element 66". Typically, an outer surface 94 of the graft extension 84 may be sealed to an inside surface 114 of the main portion 74 of attachment element 66" when the endovascular graft 10 is in a deployed state.

For some embodiments, the axial length of the branch portions 76, 76' of attachment member 66" may be sufficient to provide adequate surface area contact between an inside surface 112, 112' of branch portions 76, 76' of attachment element 66" and an outer surface 94 of a graft extension 84. Additionally, the respective inside surfaces 112, 112' of branch portions 76, 76' of attachment element 66" should provide sufficient friction to the outer surface 94 of graft extension 84 to hold the graft extension 84 in place. Expandable members, such as expandable anchor members, sinusoidal rings and the like, may be used to expand a graft extension 84 against the inside surfaces 112, 112' of branch portions 76, 76' of the attachment member 66". Varying the amount of overlap between the branch portions 76, 76' of the attachment element 66" and a graft extension 84 can allow for different effective overall graft lengths to be achieved, thereby accommodating a range of anatomical sizes with fewer distinct main body and extension dimensions than would otherwise be required. For some embodiments, the branch portions 76, 76' of attachment member 66" may have an axial length of at least about 1 cm. For some embodiments, the attachment member 66" may have an axial length of about 2 cm to about 6 cm; more specifically, about 3 cm to about 5 cm.

For some embodiments, the axial length of the main portion 74 of attachment member 66" may be sufficient to provide adequate surface area contact between an inside surface 114 of main portion 74 of attachment element 66" and an outer surface 94 of a graft extension 84. Additionally, the respective inside surface 114 of main portion 74 of attachment element 66" should provide sufficient friction to the outer surface 94 of a graft extension 84 to hold the graft extension 84 in place. Expandable members, such as expandable anchor members, sinusoidal rings and the like, may be used to expand a graft extension 84 against the inside surface 114 of main portion 74 of the attachment member 66". Varying the amount of overlap between the main portion 74 of the attachment element 66" and a graft extension 84 can allow for different effective overall graft lengths to be achieved, thereby accommodating a range of anatomical sizes with fewer distinct main body and extension dimensions than would otherwise be required. For some embodiments, the main portion 74 of attachment member 66" may have an axial length of at least about 1 cm. For some embodiments, the attachment member 66" may have an axial length of about 2 cm to about 6 cm; more specifically, about 3 cm to about 5 cm.

Figure 13:
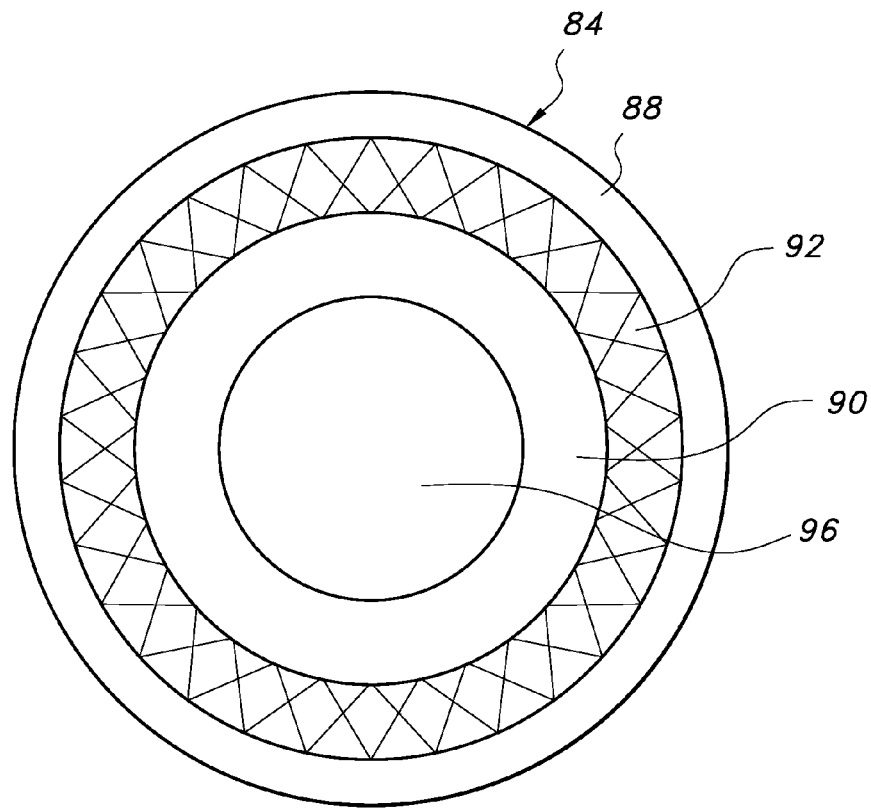
FIG. 13 is a top cross-sectional view of a graft extension having a stent attached thereto.

In some embodiments, a graft extension 84 may include an interposed self-expanding stent 92 disposed between at least one outer layer 88 and at least one inner layer 90 of supple layers of graft material, as shown in FIG. 13, which is a top cross-sectional view of a graft extension 84 having a stent 92 attached thereto. The interposed stent 92 disposed between the outer layer 88 and inner layer 90 of graft material may be formed from an elongate resilient element helically wound with a plurality of longitudinally spaced turns into an open tubular configuration. In some embodiments, the interposed stent 92 may have a winding, undulating configuration from the proximal end to the distal end. For some embodiments, the interposed stent 92 may include a superelastic alloy such as superelastic NiTi alloy. In addition, the graft material of each graft extension 84 may further include at least one axial zone of low permeability for some embodiments.

Stents may be connected to the graft extension 84 using any suitable means known in the art including, for example, any suitable connector member known in the art. Suitable stents and connector members for use in the present invention are described in U.S. Pat. No. 7,147,660, the entire contents of which are incorporated herein by reference in their entirety.

Figure 14:
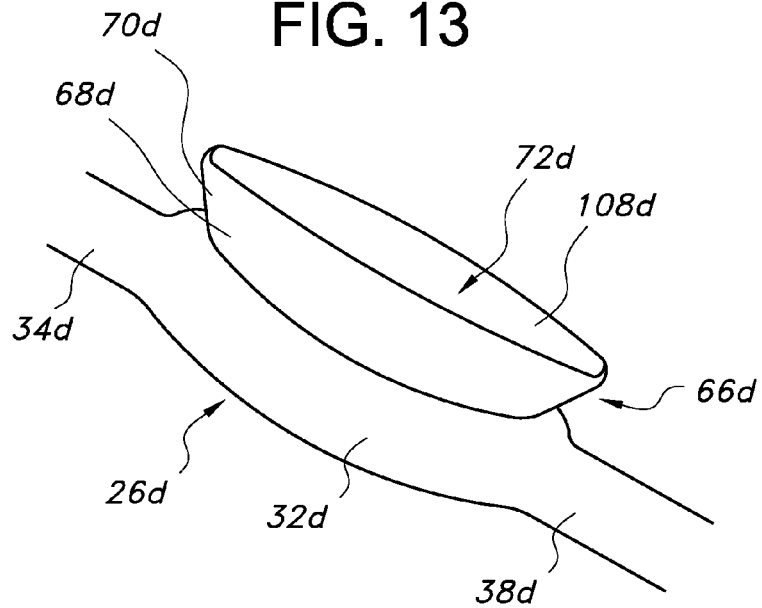
FIG. 14 is a perspective exploded view in schematic of a lateral sealing ring of the endovascular graft of FIG. 6 with an attachment member thereon.

In some embodiments, at least one lateral sealing ring 32d may have an attachment member 66d positioned thereon, as shown in FIG. 14, which is a perspective exploded view in schematic of a lateral sealing ring 32d of the endovascular graft 10d of FIG. 6 with the lateral sealing ring 32d shown having an attachment member 66d thereon and with the channels 34d and 38d of the graft 10d partially shown. The attachment member 66d may be a separate element from lateral sealing ring 32d or may be integrally formed with lateral sealing ring 32d.

In some embodiments, attachment member 66d may be a structure having a first end 68d, a second end 70d, an inside surface 108d, and a lumen 72d disposed therein, as shown in FIG. 14. In such embodiments, the first end 68d of the attachment member 66d may be positioned on lateral sealing ring 32d in coaxial relationship thereto about fenestration 26d such that lumen 72d of attachment member 66d extends from fenestration 26d in continuous relationship thereto, as shown in FIG. 14.

Figure 15:
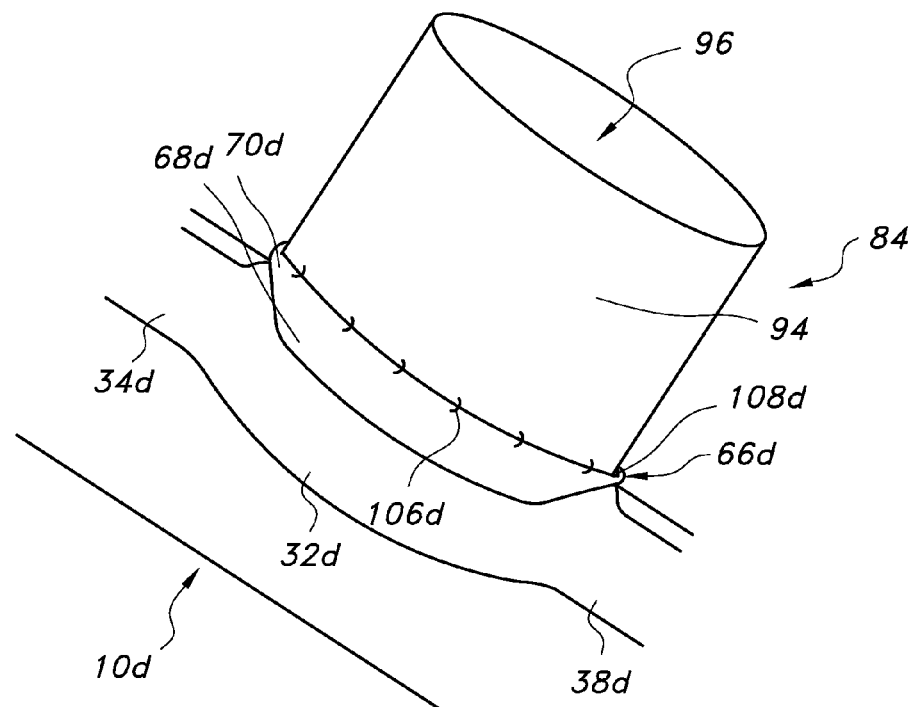
FIG. 15 is a perspective view in schematic of the lateral sealing ring of FIG. 14 shown positioned on the endovascular graft of FIG. 6 with a graft extension attached thereto by means of the attachment member shown in FIG. 14.

The attachment member 66d may be used to attach one or more graft extensions 84 to endovascular graft 10d, as further shown in FIG. 15. It will be understood that the attachment member 66d may be used to attach one or more graft extensions 84 to endovascular graft 10d in any of the ways that attachment member 66 may be used to attach a graft extension 84 to endovascular graft 10 as described herein.

Attachment member 66d may be disposed within or on, including without limitation secured to, graft extension 84 using any suitable securing means 106d known in the art, as shown in FIG. 15. Suitable securing means 106d include, for example, attachment rings, sinusoidal rings, eyelets, hooks, barbs, holes, snaps, "dog-bone" configurations, and combinations thereof. Alternative attachment means for securing the attachment member 66d to graft extension 84 include heat, compression, welding, sintering, suturing, and combinations thereof.

Figure 16:
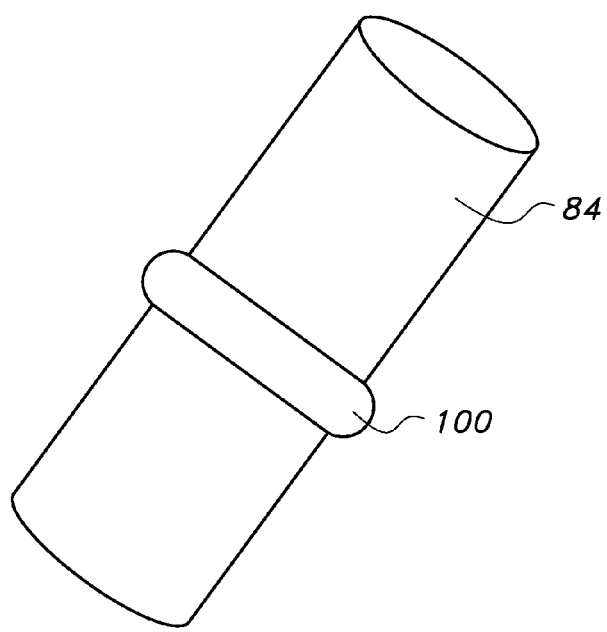
FIG. 16 is a perspective view in schematic of a graft extension having a sealing member thereon.

In some embodiments, a graft extension 84 may have at least one sealing member 100 disposed thereon, as shown in FIG. 16. In some embodiments, the sealing member 100 may be an inflatable channel or inflatable cuff. In some embodiments, a graft extension 84 may have at least one inflatable channel and/or inflatable cuff disposed thereon in any suitable configuration known in the art, including those configurations described in U.S. Pat. No. 7,150,758, the entire contents of which are incorporated herein by reference in their entirety. U.S. Pat. No. 7,147,660 discussed above also includes configurations that may be used for embodiments herein. In some embodiments, the sealing member 100 may be a sealing ring as previously described herein. In some embodiments, the sealing member 100 may be a channel as previously described herein.

Figure 17:
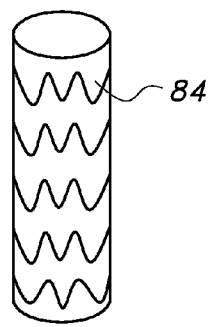
FIG. 17 is an elevational view in schematic of an extension branch graft.
Figure 17A:
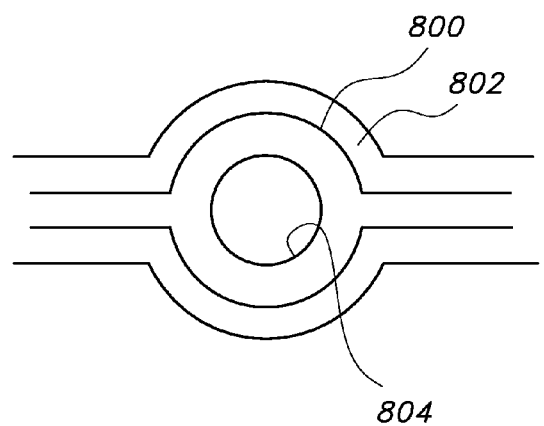
FIG. 17a is cross-sectional view of an extension branch stent member having at least one outer layer of graft material and at least one inner layer of graft material.

In some embodiments, a graft extension 84 as shown in FIG. 17 may be a self-expanding stent graft comprising a stent made of nitinol or the like, encapsulated with graft material. In some embodiments, the graft extension 84 of FIG. 17 may be a balloon-expandable stent graft comprising a stent made of stainless steel, cobalt chromium or the like, encapsulated by graft material. In some embodiments, a graft extension metal 800 as shown in FIG. 17a may be a balloon-expandable stent comprising stainless steel, cobolt chromium or the like, or a self-expanding stent made of nitinol material. In some embodiments, the graft may be multi-layered. As shown in FIG. 17a, a graft extension metal 800 may be encapsulated between two or more graft material layers including, for example, an outer layer 802, as shown in FIG. 17a and an inner layer 804, as shown in FIG. 17a.

The stent of the graft extension 84 may be interposed between an outer layer and an inner layer of graft material. The interposed stent disposed between the outer layer and inner layer of graft material may be formed from an elongate resilient element helically wound with a plurality of longitudinally spaced turns into an open tubular configuration. The helically wound stent may be configured to be a self-expanding stent or radially expandable in an inelastic manner actuated by an outward radial force from a device such as an expandable balloon or the like. Some tubular prosthesis embodiments that may be used for graft extensions 84 are discussed in U.S. Pat. No. 6,673,103 to Golds et al, which is hereby incorporated by reference in its entirety herein.

The graft extensions 84 may include a PTFE covered helical nitinol stent as described above with layers of PTFE having a variety of characteristics. The stent may be formed from an elongate resilient element which is helically wound with a plurality of longitudinally spaced turns. Some stent embodiments may be generally helical in configuration with serpentine or other regularly space undulations transverse to the helical path of the elongate stent element. The ends of the stent element may be secured to adjacent ring portions of the stent to avoid exposure of element ends to either PTFE graft material or possible patient tissues. The stent element may be a continuous element from one end of the extension to the other end thereof. The ends of the elongate element may be secured to adjacent ring members by any suitable means such as adhesive bonding, welding such as laser welding, soldering or the like. For some embodiments, the stent element may have a transverse dimension or diameter of about 0.005 inch to about 0.015 inch.

For some embodiments of graft extension 84, layers of materials having different properties may be used in combination to achieve a desired clinical performance. For example, some layers of PTFE covering the stent may be permeable, semi-permeable or substantially non-permeable depending on the desired performance and material properties. The layers may be applied by a variety of methods and have a variety of configurations. For example, some layer embodiments may include extruded tubular structures applied axially over a mandrel or subassembly. Some layer embodiments may be applied by wrapping layers circumferentially or wrapping tapes or ribbons in an overlapping helical pattern. For some embodiments, the outer layer may be made from or include a semi-permeable or substantially non-permeable PTFE layer, and the inner layer may be made of or include a permeable layer of PTFE.

The graft extensions 84 may be made by forming the layers of material together with the stent over a mandrel, such as a cylindrical mandrel (not shown). Once the innermost layer of the extension has been wrapped or otherwise disposed about a shaped mandrel, a helical nitinol stent may be placed over the innermost layered PTFE layer and underlying mandrel. One or more additional layers of low permeability PTFE film or PTFE film having substantially no permeability that does not have the traditional node fibril microstructure may be wrapped or otherwise added over the exterior of the stent. The mandrel may then be covered with a flexible tube such that the film and stent is sandwiched under pressure and sintered so as to raise the temperature for the PTFE material to undergo a melt transformation in order to lock in its geometry and strength. The flexible tube (a manufacturing aid not shown) is removed from over the device and the resultant extension is removed from the mandrel. Additional details of the graft extensions, including delivery methods and systems, may be found in commonly owned U.S. Patent Application Publication No. 2009/0099649 A1 to Chobotov et al., the contents of which are incorporated herein by reference.

Figure 18:
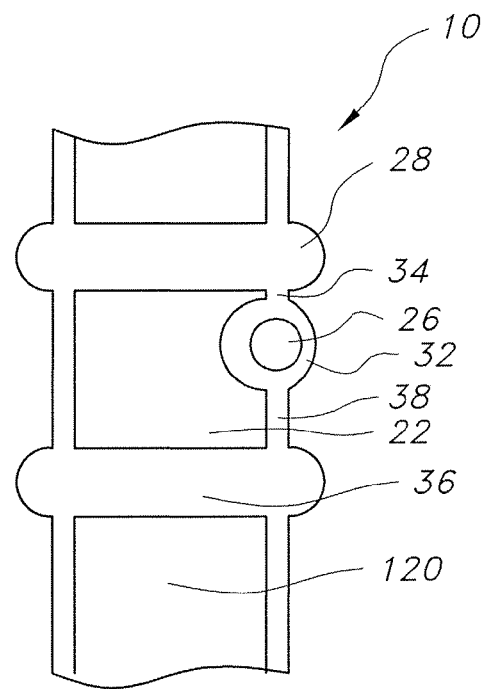
FIG. 18 is an elevational view in schematic of a representative inflatable graft section with a lateral fenestration.

The endovascular graft 10 as shown in FIG. 18 includes fenestration 26 which extends through the wall 22 of the graft portion 120. The endovascular graft 10 has proximal and distal inflatable rings 28, 36, lateral sealing ring 32, channels 34, 38, and a fenestration 26 in the graft portion 120, as shown in FIG. 18.

Figure 19:
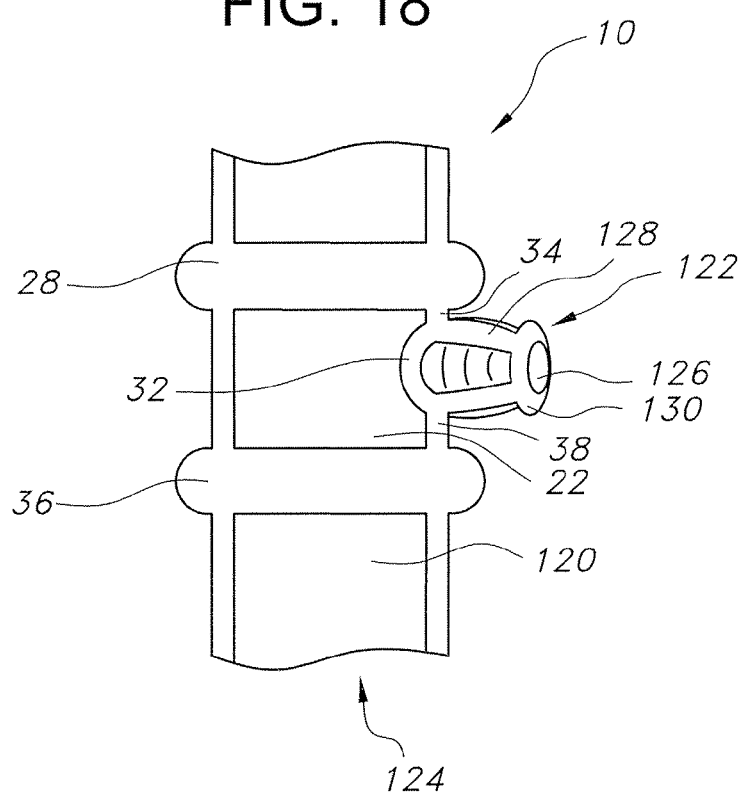
FIG. 19 is an elevational view in schematic of a representative inflatable graft section with a lateral branch portion.

The endovascular graft 10 as shown in FIG. 19 includes a lateral branch 122 which extends from the wall 22 of the graft portion 120. The endovascular graft 10 has proximal and distal inflatable rings 28, 36, lateral sealing ring 32, channels 34, 38, and a conduit 124 in the graft portion 120, as shown in FIG. 19, as well as a conduit 126 in the lateral branch 122. The lateral branch 122 may include inflatable sealing rings 128, 130 thereon, as shown in FIG. 19.

Figure 20:
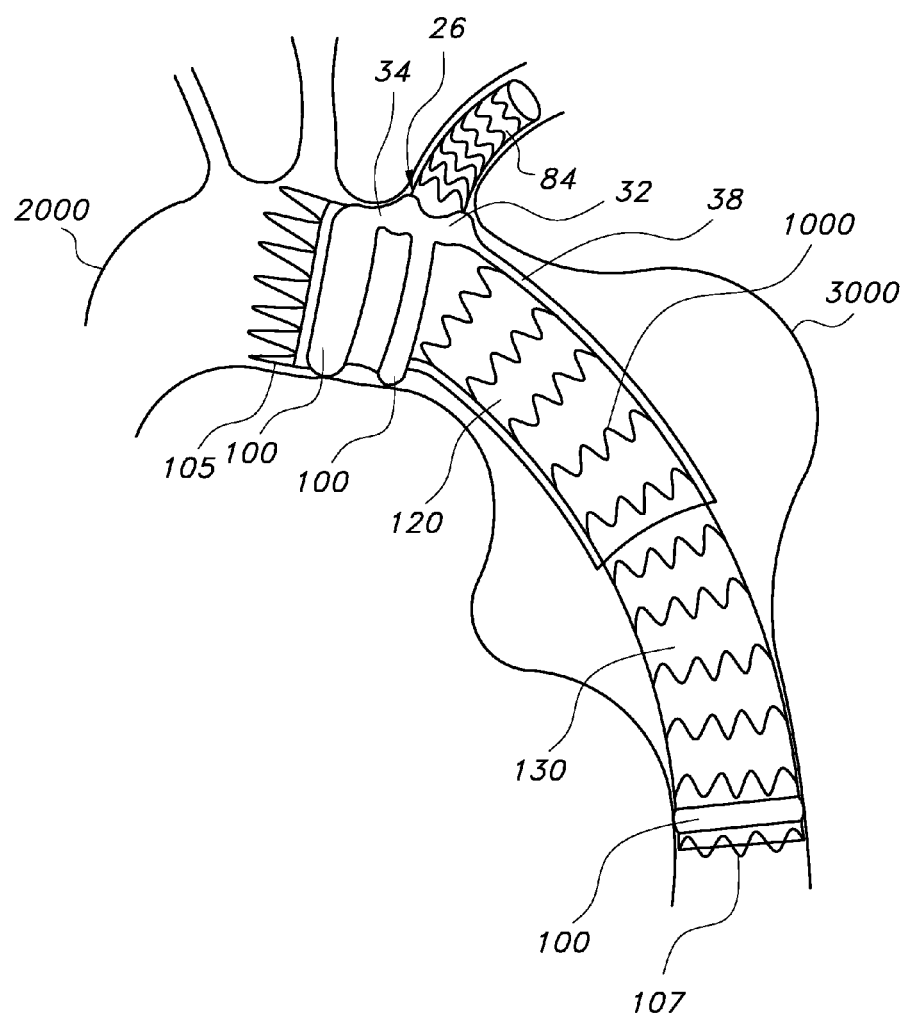
FIG. 20 is a perspective view in schematic of a graft with a lateral sealing ring and fenestration of FIG. 2 with a graft extension of FIG. 17 positioned within the fenestration and lateral seal ring.
Figure 21:
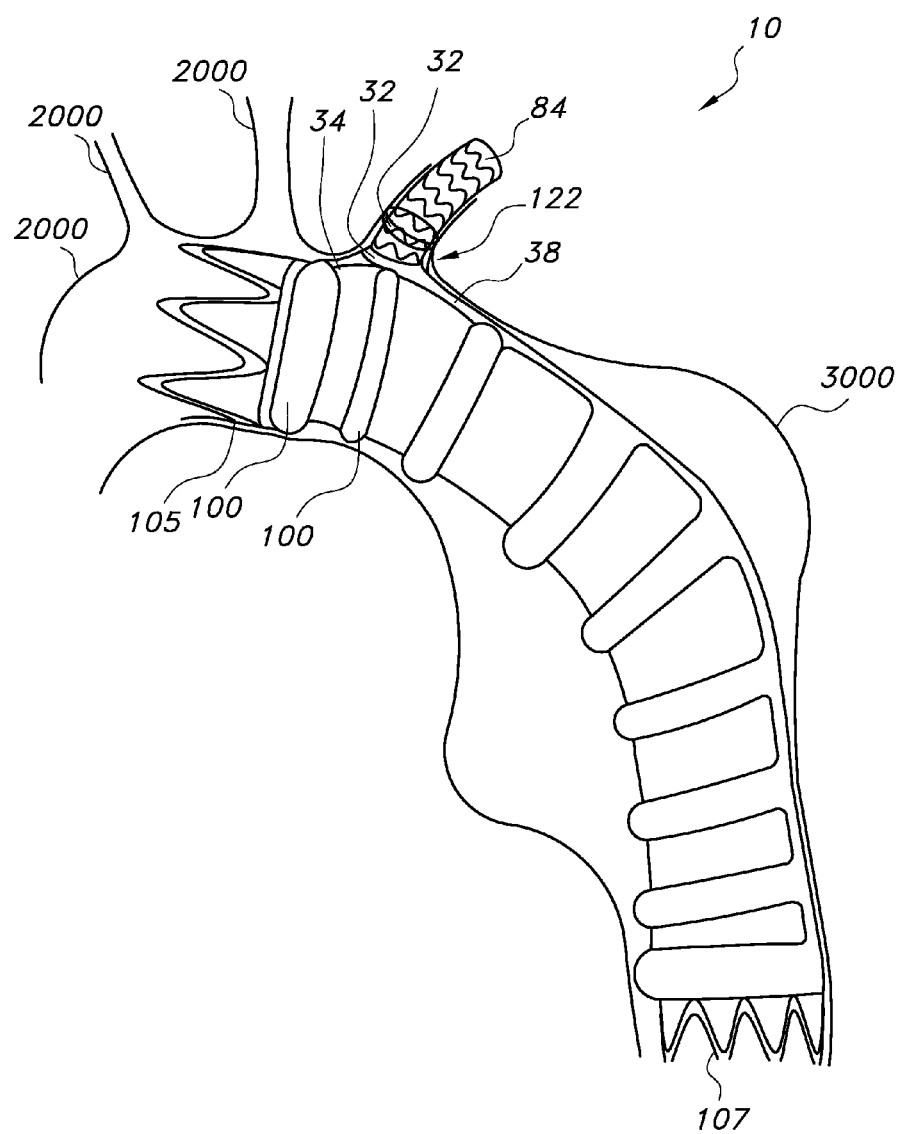
FIG. 21 is a perspective view in schematic of an embodiment of the endovascular graft of FIG. 20, the endovascular graft being shown as having a lateral branch portion of FIG. 19 with a graft extension of FIG. 17 positioned within the lateral branch portion.

An embodiment of the endovascular graft 10 is possible which has a graft extension 84, which is a lateral extension graft, positioned within the fenestration 26 as shown in FIG. 20. In such an embodiment, the graft extension 84, which is a lateral extension graft, can be positioned after placement of the main graft body portion 120. The lateral sealing ring 32 encircles the graft extension 84, as shown in FIG. 20. In such an embodiment a blood path is formed through the lateral fenestration 26 and graft extension 84. In such an embodiment a blood path is formed through the lateral fenestration 26 and graft extension 84. FIG. 20 shows a modular hybrid thoracic stent graft where two stent graft bodies 120, 130 are positioned. Varying the amount of overlap between the main body portion 120 and a second graft body 130 can allow for different effective overall graft lengths to be achieved, thereby accommodating a range of anatomical sizes with fewer distinct main body and second graft body dimension that would otherwise be required. In some embodiments, the hybrid graft bodies have one or more sealing members 100, such as inflatable channels, and one or more sealing rings 32 and one or more interposed stents including, for example, a proximal anchor 105 and a distal anchor 107. The interposed stent may have a winding, undulating configuration from the proximal end to the distal end. For some embodiments, the interposed stent may be secured to the graft bodies 120, 130 using any suitable securing means, including heat, compression, welding, sintering, suturing and combinations thereof. The graft 10 may include a helical wound stent 1000 as shown in FIG. 21. The present invention, however, is not so limited. For example, previously described networks of inflatable channels or another suitable networks of inflatable channels may suitable be used in conjunction with or to replace the stent 1000. The graft of FIG. 20 may include an axial channel 34 and an axial channel 38.

An embodiment of the endovascular graft 10 is possible where the main graft body 120 has a lateral branch portion 122. Lateral seal rings 32 can be positioned along lateral branch portion 122 to aide in graft opening. A graft extension 84, which may be a lateral extension graft, as shown in FIG. 21 can be positioned in the lateral branch portion 122. In such an embodiment, the graft extension 84, which is a lateral extension graft in FIG. 21, can be positioned after placement of the main graft body portion 120. The lateral sealing rings 32 of the lateral branch portion 122 encircle the graft extension 84, as shown in FIG. 21. In such an embodiment a blood path is formed through the lateral branch portion 122 and graft extension 84. In some embodiments, the endovascular graft 10 shown in FIG. 21 may have one or more sealing members 100, such as inflatable channels, and one or more sealing rings 32 and one or more interposed stents including, for example, a proximal anchor 105 and a distal anchor 107. The interposed stent may have a winding, undulating configuration from the proximal end to the distal end. For some embodiments, the interposed stent may be secured to the graft using any suitable securing means, including heat, compression, welding, sintering, suturing and combinations thereof. Graft 10 shown in FIG. 21 may include axial channels 34 and 38.

Figure 22:
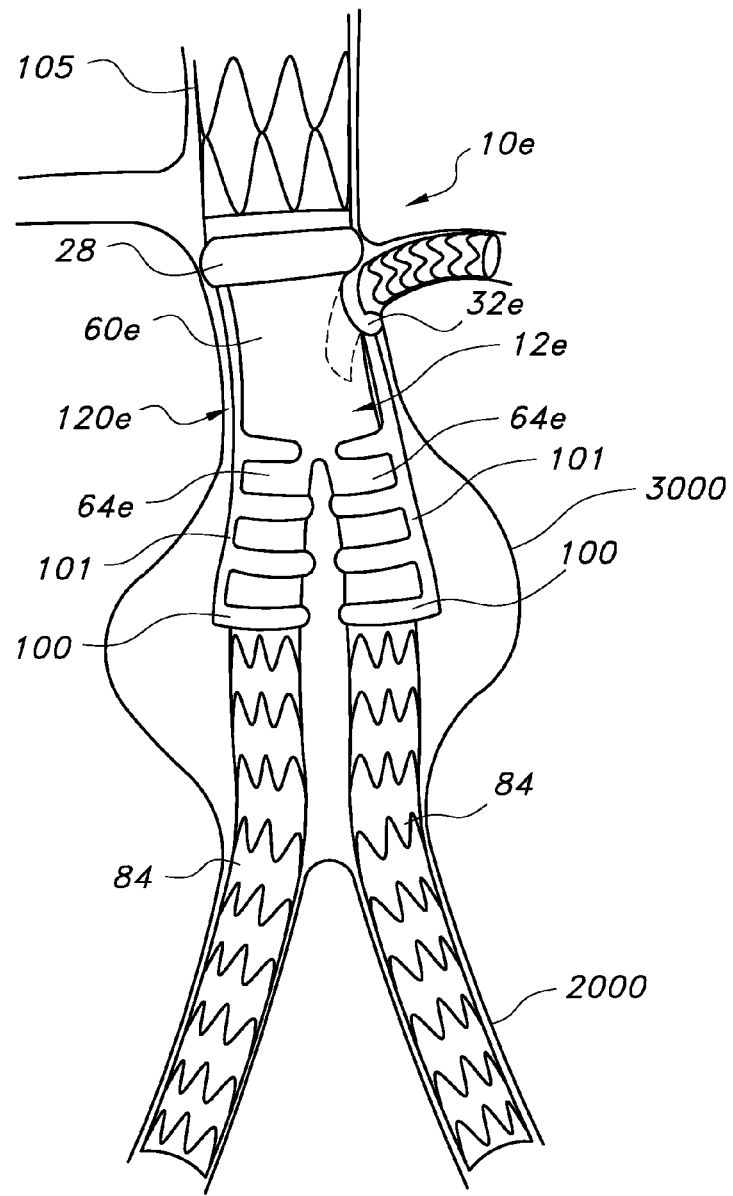
FIG. 22 is a perspective view in schematic of a graft with a lateral sealing ring and fenestration of FIG. 6 with a graft extension of FIG. 17 positioned within the fenestration and lateral seal ring.

An embodiment of an endovascular graft 10e is shown in FIG. 22. Elements illustrated in FIG. 22 which correspond to elements illustrated in FIGS. 1 and 2 have, in FIG. 22, the same reference numerals as in FIGS. 1 and 2, with the addition of the suffix e. In this embodiment, the endovascular graft 10e includes a tubular structure 12e which is bifurcated. Consequently, the tubular structure 12e includes a trunk portion 60e and a pair of leg portions 64e which extend from the trunk portion 60e. In such an embodiment, the branch extension 84, which may be a lateral extension graft as shown in FIG. 22, can be positioned after placement of the main graft body portion 120e. The lateral sealing ring 32e encircles the graft extension 84, as shown in FIG. 22. In such an embodiment a blood path is formed through the lateral fenestration 32e and graft extension 84. Graft extensions 84 may also extend from legs 64e. The graft 10e may have a proximal anchor 105 and a sealing member 28. The graft 10e shown in FIG. 22 may have one or more sealing members 100 thereon and axial channels 101.

It will be understood that a graft extension 84, as shown in FIG. 22, may be positioned within a lateral sealing ring 32d, as shown in FIG. 6. In such an embodiment, the lateral sealing ring 32d may encircle the graft extension 84.

Fenestration 26 as shown in FIG. 18 can be used with inflatable grafts that are bifurcated or tubular in shape, or with inflatable and wire wound hybrid grafts that are bifurcated, as shown in FIG. 22, or tubular in shape, as shown in FIG. 20.

One or more lateral branch portion 122 as shown in FIG. 19 can be used with inflatable grafts that are bifurcated or tubular in shape, as shown in FIG. 21, or with inflatable and wire wound hybrid grafts that are bifurcated or tubular in shape.

Figure 23:
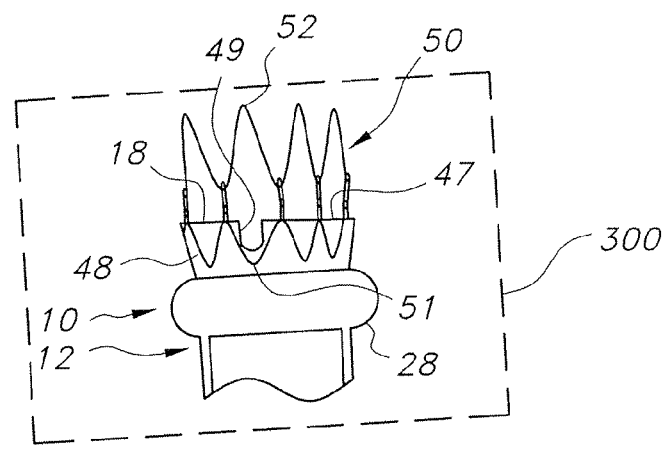
FIG. 23 shows a graft end portion which may be disposed with or on any of the grafts of the present invention, including those grafts shown in FIGS. 1, 2, and 6.

FIG. 23, which is also referred to as "old FIG. 8," shows how a graft flap with a stent disposed within or on the graft flap may be disposed within or on an inflatable member, such as a sealing cuff of the presented invention.

In some embodiments, the end 300 or any part thereof which is shown in FIG. 23, which is also referred to as old FIG. 8, may be added to any of the grafts 10, 10d, 10e of the present invention, including to both or either of the ends 400 shown in FIG. 1, to both or either of the ends 500 shown in FIG. 2, and to any or all of the ends 600 shown in FIG. 6.

Figure 24:
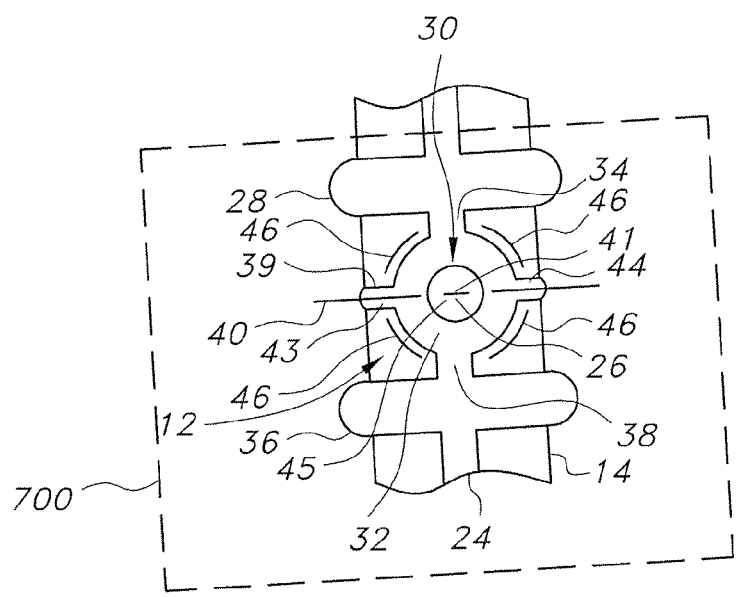
FIG. 24 shows a graft portion which may be disposed with or on any of the grafts of the present invention, including the graft shown in FIG. 1. Corresponding reference characters indicate corresponding elements throughout the several views of the drawings.

In some embodiments, a graft portion 700 as shown in FIG. 24, which is also referred to as old FIG. 4, may be used on or in conjunction with a graft as shown in FIG. 1.

It will be understood that the drawings herein shown an aneurysm 3000.

A sealing member 100 for use in the present invention, including any of the inflatable channels and/or inflatable cuffs and/or sealing rings described herein, may be filled during deployment of a graft of the present invention with any suitable inflation material. The inflation material may be used to provide outward pressure or a rigid structure from within the sealing member. Biocompatible gases, liquids, gels or the like may be used, including curable polymeric materials or gels. Some embodiments may use inflation materials formed from glycidyl ether and amine materials, as discussed in U.S. patent application Ser. No. 11/097,467, U.S. Patent Application Publication No. 2006/0222596 A1, filed Apr. 1, 2005, and entitled "Non-Degradable, Low-Swelling, Water Soluble Radiopaque Hydrogel Polymer" to Askari and Whirley, the entire contents of which are incorporated by reference herein in their entirety. Some inflation material embodiments may include an in situ-formed hydrogel polymer having a first amount of diamine and a second amount of polyglycidyl ether wherein each of the amounts are present in an amount to produce an in situ formed hydrogel polymer that is biocompatible and has a cure time after mixing of about 10 seconds to about 30 minutes and wherein the volume of the hydrogel polymer swells less than 30 percent after curing and hydration. Some embodiments of the inflation material may include radiopaque materials such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter of the present invention may be directly inserted into the patient's access vessel by either arteriotomy or percutaneous puncture. Once the delivery sheath or sheaths have been properly positioned, an endovascular delivery catheter or system, typically containing an endovascular prosthesis such as but not limited to the grafts or prostheses of the present invention, may then be advanced over a guidewire through the delivery sheath and into the patient's vasculature.

Once an endovascular graft 10, 10d, 10e of the invention has been partially or fully deployed, a proximal inflatable cuff may then be filled through an inflation port with inflation material injected through an inflation tube of the endovascular delivery system which may serve to seal an outside surface of the inflatable cuff to the inside surface of a vessel such as a blood vessel 2000. The remaining network of inflatable channels may also be filled with pressurized inflation material at the same time which provides a more rigid frame like structure to the inflatable graft. For some embodiments, the inflation material may be a biocompatible, curable or hardenable material that may cured or hardened once the network of inflatable channels are filled to a desired level of material or pressure within the network or after passage of a predetermined period of time. Some embodiments may also employ radiopaque inflation material to facilitate monitoring of the fill process and subsequent engagement of graft extensions (not shown). The material may be cured by any of the suitable methods discussed herein including time lapse, heat application, application of electromagnetic energy, ultrasonic energy application, chemical adding or mixing or the like. Some embodiments for the inflation material that may be used to provide outward pressure or a rigid structure from within the inflatable cuff or network of inflatable channels may include inflation materials formed from glycidyl ether and amine materials. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

U.S. Pat. No. 7,147,660 discussed above also includes inflation material embodiments that may be used for embodiments discussed herein.

U.S. Pat. Nos. 6,395,019 and 8,241,346 are hereby incorporated by reference herein in their entirety.

Further details of the endovascular prosthesis/graft and/or graft extensions may be found in commonly owned U.S. Pat. Nos. 6,395,019; 7,081,129; 7,147,660; 7,147,661; 7,150,758; 7,651,071; 7,766,954 and 8,167,927 and commonly owned U.S. Published Application No. 2009/0099649, the contents of all of which are incorporated herein by reference in their entirety. Details for the manufacture of the endovascular prosthesis/graft may be found in commonly owned U.S. Pat. Nos. 6,776,604; 7,090,693; 7,125,646; 7,147,455; 7,678,217 and 7,682,475, the contents of all of which are incorporated herein by reference in their entirety. Useful inflation materials for the inflatable graft may be found in may be found in commonly owned U.S. Published Application No. 2005/0158272 and 2006/0222596, the contents of all of which are incorporated herein by reference in their entirety. Further details, including but not limited to methods, catheters and systems, for deployment of endovascular prostheses are disclosed in commonly owned U.S. Pat. Nos. 6,761,733 and 6,733,521; commonly owned U.S. Patent Application Publication Nos. 2006/0009833 and 2009/0099649; and commonly owned U.S. Provisional Application Nos. 61/660,103, 61/660,105 and 61/711,797; all of which are incorporated by reference herein in their entirety.

Useful stent, anchor, and connector rings may be made from or include any biocompatible material, including metallic materials, such as but not limited to, nitinol (nickel titanium), cobalt-based alloy such as Elgiloy, platinum, gold, stainless steel, titanium, tantalum, niobium, and combinations thereof.

Useful graft materials for the endovascular prosthesis/graft include, but are not limited, polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrenebutadiene copolymers; polyethers; such as fully or partially halogenated polyethers; and copolymers and combinations thereof. In some embodiments, the graft materials are non-textile graft materials, e.g., materials that are not woven, knitted, filament-spun, etc. that may be used with textile grafts. Such useful graft material may be extruded materials. Particularly useful materials include porous polytetrafluoroethylene without discernable node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. Such PTFE layers may lack distinct, parallel fibrils that interconnect adjacent nodes of ePTFE, typically have no discernable node and fibril microstructure when viewed at a magnification of up to 20,000. A porous PTFE layer having no or substantially no fluid permeability may have a Gurley Number of greater than about 12 hours, or up to a Gurley Number that is essentially infinite, or too high to measure, indicating no measurable fluid permeability. Some PTFE layers having substantially no fluid permeability may have a Gurley Number at 100 cc of air of greater than about $10^6$ seconds. The Gurley Number is determined by measuring the time necessary for a given volume of air, typically, 25 cc, 100 cc or 300 cc, to flow through a standard 1 square inch of material or film under a standard pressure, such as 12.4 cm column of water. Such testing maybe carried out with a Gurley Densometer, made by Gurley Precision Instruments, Troy, N.Y. Details of such useful PTFE materials and methods for manufacture of the same may be found in commonly owned U.S. Patent Application Publication No. 2006/0233991, the contents of which are incorporated herein by reference in their entirety. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter of the present invention may be directly inserted into the patient's access vessel by either arteriotomy or percutaneous puncture. Once the delivery sheath or sheaths have been properly positioned, an endovascular delivery catheter or system, typically containing an endovascular prosthesis such as but not limited to the grafts or prostheses of the present invention, may then be advanced over a guidewire through the delivery sheath and into the patient's vasculature.

In one embodiment, a method for delivering and deploying the grafts of the present invention may include: deploying the main body graft of TAA or AAA device with one or more lateral fenestrations by using, for example, standard endovascular procedures, obtain guidewire access through the main aorta. Details of such techniques, including but not limited to methods, catheters and systems, for deployment of endovascular prostheses are disclosed in commonly owned U.S. Pat. Nos. 6,761,733 and 6,733,521; commonly owned U.S. Patent Application Publication Nos. 2006/0009833 and 2009/0099649; and commonly owned U.S. Provisional Application Nos. 61/660,103, 61/660,105 and 61/711,797; all of which are incorporated by reference herein in their entirety. The main graft is advanced axially to an intended deployment site (longitudinal position). Radiopaque markers may be to aid in rotating and aligning the position of the lateral fenestration to supply blood to the anatomical branch vessel. After aligning the graft at its intended position, a delivery sheath of the delivery catheter or system is then typically removed. The stent graft is then in its final position for deployment. The stent graft may be axially or rotationally adjusted until the stent of the main stent graft is deployed. The stent graft is then in its final position for deployment. The sealing rings or channels of the main graft may then be filled with polymer. After aligning and filling the graft at its intended position, a delivery catheter or system is then typically removed. As a result, the sealing rings proximal and distal to branch vessel direct blood through main body graft and into anatomical branch vessel.

In an alternate method, a stent graft with a lateral branch vessel may be used and positioned. The main body graft of TAA or AAA device with one or more lateral fenestrations may be deployed and deploy extension graft to direct flow into the anatomical branch vessels. Using standard endovascular techniques it is desirable to cannulate both the fenestration and target anatomical branch vessel with a guidewire. Then, the extension graft is advanced over a guidewire to deploy an extension graft that is partially deployed in the lateral fenestration and partially deployed within the anatomical branch vessel. A seal is created between the lateral fenestration sealing ring and graft extension, and the graft extension in apposition with the anatomical branch vessel. The result is lateral fenestration with sealing ring and extension graft direct blood through the main body graft and into anatomical branch vessel. The result is a lateral fenestration with a sealing ring and an extension graft that direct blood through the main body graft and into anatomical branch vessel.

In yet another alternate method a guidewire access may be obtained first through the main aorta and target branch vessel. Using standard endovascular procedures, guidewire access through the main aorta is obtained. Using standard endovascular procedures, guidewire access through the main aorta and into the target anatomical branch vessel is also obtained. The guidewires may back loaded into the delivery system with dual guideways (not shown). One guideway is through the main body lumen. The additional guideway is through the fenestration then into main body lumen. The stent graft may be then advanced to intended deployment site (longitudinal position). The use radiopaque markers may aid any rotating of the stent graft and aligning position of the lateral fenestration or branch portion (radial position) to supply blood to the anatomical branch vessel. Following proper alignment, the delivery sheath of the delivery catheter or system is retracted. After confirming proper positioning, the stent graft may be deployed into final position, followed by filling the graft with polymer. The result is that sealing rings proximal and distal to branch vessel direct blood through main body graft and into anatomical branch vessel. Fenestration and anatomical branch vessel are already cannulated.

In yet another alternate method to, a stent graft with a lateral branch vessel may used and positioned. The method includes deploying the main body graft of TAA or AAA device with one or more lateral fenestrations and deploy extension graft to direct flow into the anatomical branch vessels. Again, standard endovascular techniques may be used to deploy extension graft. The extension graft may be advanced over the guidewire to deploy an extension graft that is partially deployed in the lateral fenestration and partially deployed within the anatomical branch vessel. A seal is created between the lateral fenestration sealing ring and graft extension, and the graft extension in apposition with the anatomical branch vessel. The result is a lateral fenestration with a sealing ring and an extension graft that direct blood through the main body graft and into anatomical branch vessel.

In still another alternate method, a stent graft with a lateral branch vessel may be used and positioned by any of the above described techniques.

For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter of the present invention may be directly inserted into the patient's access vessel by either arteriotomy or percutaneous puncture. Once the delivery sheath or sheaths have been properly positioned, an endovascular delivery catheter or system, typically containing an endovascular prosthesis such as but not limited to the grafts or prostheses of the present invention, may then be advanced over a guidewire through the delivery sheath and into the patient's vasculature.

In one embodiment, a method for delivering and deploying the grafts of the present invention may include: deploying the main body graft of TAA or AAA device with one or more lateral fenestrations by using, for example, standard endovascular procedures, obtain guidewire access through the main aorta. Details of such techniques, including but not limited to methods, catheters and systems, for deployment of endovascular prostheses are disclosed in commonly owned U.S. Pat. Nos. 6,761,733 and 6,733,521; commonly owned U.S. Patent Application Publication Nos. 2006/0009833 and 2009/0099649; and commonly owned U.S. Provisional Application Nos. 61/660,103, 61/660,105 and 61/711,797; all of which are incorporated by reference herein in their entirety. The main graft is advanced axially to an intended deployment site (longitudinal position). Radiopaque markers may be to aid in rotating and aligning the position of the lateral fenestration to supply blood to the anatomical branch vessel. The stent graft is then in its final position for deployment. The stent graft may be axially or rotationally adjusted until the stent of the main stent graft is deployed. The stent graft is then in its final position for deployment. The sealing rings or channels of the main graft may then be filled with polymer. After aligning and filling the graft at its intended position, a delivery catheter or system is then typically removed. As a result, the sealing rings proximal and distal to branch vessel direct blood through main body graft and into anatomical branch vessel. The stent graft may be axially or rotationally adjusted until the stent of the main stent graft is deployed. The stent graft is then in its final position for deployment. The sealing rings or channels of the main graft may then be filled with polymer. After aligning and filling the graft at its intended position, a delivery catheter or system is then typically removed. As a result, the sealing rings proximal and distal to branch vessel direct blood through main body graft and into anatomical branch vessel.

In an alternate method, a stent graft with a lateral branch vessel may be used and positioned. The main body graft of TAA or AAA device with one or more lateral fenestrations may be deployed and deploy extension graft to direct flow into the anatomical branch vessels. Using standard endovascular techniques it is desirable to cannulate both the fenestration and target anatomical branch vessel with a guidewire. Then, the extension graft is advanced over a guidewire to deploy an extension graft that is partially deployed in the lateral fenestration and partially deployed within the anatomical branch vessel. A seal is created between the lateral fenestration sealing ring and graft extension, and the graft extension in apposition with the anatomical branch vessel. The result is a lateral fenestration with a sealing ring and extension graft direct blood through the main body graft and into anatomical branch vessel.

In yet another alternate method a guidewire access may be obtained first through the main aorta and target branch vessel.

Using standard endovascular procedures, guidewire access through the main aorta is obtained. Using standard endovascular procedures, guidewire access through the main aorta and into the target anatomical branch vessel is also obtained. The guidewires may back loaded into the delivery system with dual guideways (not shown). One guideway is through the main body lumen. The additional guideway is through the fenestration then into main body lumen. The stent graft may be then advanced to intended deployment site (longitudinal position). The use radiopaque markers may aid any rotating of the stent graft and aligning position of the lateral fenestration or branch portion (radial position) to supply blood to the anatomical branch vessel. Following proper alignment, the delivery sheath of the delivery catheter or system is retracted. After confirming proper positioning, the stent graft may be deployed into final position, followed by filling the graft with polymer. The result is that sealing rings proximal and distal to branch vessel direct blood through main body graft and into anatomical branch vessel. Fenestration and anatomical branch vessel are already cannulated.

In yet another alternate method to, a stent graft with a lateral branch vessel may used and positioned. The method includes deploying the main body graft of TAA or AAA device with one or more lateral fenestrations and deploy extension graft to direct flow into the anatomical branch vessels. Again, standard endovascular techniques may be used to deploy extension graft. The extension graft may be advanced over the guidewire to deploy an extension graft that is partially deployed in the lateral fenestration and partially deployed within the anatomical branch vessel. A seal is created between the lateral fenestration sealing ring and graft extension, and the graft extension in apposition with the anatomical branch vessel. The result is a lateral fenestration with a sealing ring and an extension graft that direct blood through the main body graft and into anatomical branch vessel.

In still another alternate method, a stent graft with a lateral branch vessel may be used and positioned by any of the above described techniques.

In some embodiments, a main body graft of TAA or AAA device with one or more lateral fenestrations is deployed using, without limitation, the following steps: a) Using standard endovascular procedures, guidewire access through the main aorta is obtained; b) Advance to an intended deployment site (longitudinal position); c) Use radiopaque markers to rotate and align position of the lateral fenestration to supply blood to the anatomical branch vessel; d) retract a sheath; e) deploy stent graft into final position; and f) fill the graft with a polymer. As a result, the sealing rings proximal and distal to branch vessel direct blood through main body graft and into anatomical branch vessel.

In some embodiments, a stent graft with a lateral branch vessel is used and positioned by deploying a main body graft of TAA or AAA device with one or more lateral fenestrations and deploy extension graft to direct flow into the anatomical branch vessels.

In some embodiments, standard endovascular techniques may be used to cannulate both the fenestration and target anatomical branch vessel with a guidewire. In such embodiments, an extension graft is advanced over a guidewire to deploy an extension graft that is partially deployed in the lateral fenestration and partially deployed within an anatomical branch vessel. A seal is created between the lateral fenestration sealing ring and graft extension, and the graft extension in apposition with the anatomical branch vessel. The result is that the lateral fenestration with sealing ring and extension graft direct blood through the main body graft and into the anatomical branch vessel.

In some embodiments, guidewire access may be obtained first through the main aorta and target branch vessel. By using standard endovascular procedures, guidewire access through the main aorta may be obtained. By using standard endovascular procedures, guidewire access through the main aorta and into the target anatomical branch vessel may be obtained. The guidewires may be back loaded into the delivery system with dual guideways. One guideway may be through the main body lumen. Additional guideway may be through the fenestration then into main body lumen and then advance to an intended deployment site (longitudinal position). Radiopaque markers may then be used to rotate and align position of the lateral fenestration or branch portion (radial position) to supply blood to the anatomical branch vessel. A sheath may then be retracted, and the stent-graft deployed into the final position. The graft may then be filled with a polymer. As a result, sealing rings proximal and distal to branch vessel direct blood through main body graft and into anatomical branch vessel. In such embodiments, the fenestration and anatomical branch vessel are already cannulated.

In some embodiments, a main body graft of TAA or AAA device with one or more lateral fenestrations is deployed and the extension graft is deployed to direct flow into the anatomical branch vessels.

In some embodiments, standard endovascular techniques to deploy extension graft may be used. In such embodiments, a extension graft may be advanced over the guidewire to deploy an extension graft that is partially deployed in the lateral fenestration and partially deployed within the anatomical branch vessel. A seal is created between the lateral fenestration sealing ring and graft extension, and the graft extension in apposition with the anatomical branch vessel. As a result, lateral fenestration with sealing ring and extension graft direct blood through the main body graft and into anatomical branch vessel.

In some embodiments, a stent graft with a lateral branch vessel is used and positioned.

While the invention has been described by reference to certain embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An endovascular graft comprising:
   a tubular structure having a first end and a second end, said tubular structure having a wall which defines a lumen between said first end and said second end;
   a fenestration located between said first end and said second end to extend through said wall of said tubular structure; and
   a sealing ring circumferentially disposed within or onto said tubular structure, said sealing ring being adjacent to said fenestration;
   wherein said sealing ring circumferentially disposed within or onto said tubular structure defines a circumferential sealing ring;
   said endovascular graft further comprising an arcuate intermediate sealing ring circumferentially disposed within or on said tubular structure, said intermediate sealing ring having a longitudinal plane which has an axial position relative to said tubular structure such that said axial position of said longitudinal plane is substantially the same as an axial position of a center of said fenestration relative to said tubular structure, said intermediate sealing ring having a first end and a second end, said intermediate sealing ring having a circumferential gap between said first end and said second end of said intermediate sealing ring, said intermediate sealing ring being circumferentially positioned relative to said fenestration such that said fenestration is within said gap; wherein said intermediate sealing ring is inflatable;

said endovascular graft further comprising an inflatable lateral sealing ring disposed within or on said tubular structure in coaxial relation to said fenestration such that said fenestration is encircled by said lateral sealing ring; and said lateral and said intermediate sealing ring being connected to one another for communication therebetween such that inflation of one of said lateral sealing ring and said intermediate sealing ring provides inflation of the other of said lateral sealing ring and said intermediate sealing ring.

2. An endovascular graft according to claim 1, wherein said sealing ring that is circumferentially disposed within or on said tubular structure is upstream of said fenestration and defines a proximal sealing ring, said proximal sealing ring being inflatable, said endovascular graft further comprising a distal sealing ring circumferentially disposed within or on said tubular structure, said distal sealing ring being adjacent to and downstream of said fenestration, said distal sealing ring being inflatable, said proximal sealing ring and said distal sealing ring being connected to one another for communication therebetween such that inflation of one of said proximal sealing ring and said distal sealing ring provides inflation of the other of said proximal sealing ring and said distal sealing ring.

3. An endovascular graft according to claim 2, and further comprising a channel disposed within or on said tubular structure, said channel being connected to said proximal sealing ring and said distal sealing ring in communication therewith to provide said communication between said proximal sealing ring and said distal sealing ring.

4. An endovascular graft according to claim 1, wherein said circumferential sealing ring is inflatable, said circumferential sealing ring and said lateral sealing ring being connected to one another for communication therebetween such that inflation of one of said circumferential sealing ring and said lateral sealing ring provides inflation of the other of said circumferential sealing ring and said lateral sealing ring.

5. An endovascular graft according to claim 4, and further comprising a channel disposed within or on said tubular structure, said channel being connected to said circumferential sealing ring and said lateral sealing ring in communication therewith to provide said communication between said circumferential sealing ring and said lateral sealing ring.

6. An endovascular graft according to claim 4, wherein said circumferential sealing ring is upstream of said fenestration, said circumferential sealing ring defining a proximal sealing ring, said endovascular graft further comprising a distal sealing ring circumferentially disposed within or on said tubular structure, said distal sealing ring being adjacent to and downstream of said fenestration, said distal sealing ring being inflatable, said distal sealing ring and said lateral sealing ring being connected to one another for communication therebetween such that inflation of one of said distal sealing ring and said lateral sealing ring provides inflation of the other of said distal sealing ring and said lateral sealing ring.

7. An endovascular graft according to claim 6, and further comprising a channel disposed within or on said tubular structure, said channel being connected to said distal sealing ring and said lateral sealing ring in communication therewith to provide said communication between said distal sealing ring and said lateral sealing ring.

8. An endovascular graft according to claim 1, wherein said circumferential sealing ring is inflatable, said circumferential sealing ring and said intermediate sealing ring being connected to one another for communication therebetween such that inflation of one of said circumferential sealing ring and said intermediate sealing ring provides inflation of the other of said circumferential sealing ring and said intermediate sealing ring.

9. An endovascular graft according to claim 8, and further comprising a channel disposed within or on said tubular structure, said channel being connected to said circumferential sealing ring and said intermediate sealing ring in communication therewith to provide said communication between said circumferential sealing ring and said intermediate sealing ring.

10. An endovascular graft according to claim 1, and further comprising a radiopaque marker disposed within or on said tubular structure.

11. An endovascular graft according to claim 10, wherein said radiopaque marker is adjacent to said fenestration.

12. An endovascular graft according to claim 1, wherein said first or second end of said tubular structure is defined by a transverse edge, said tubular structure having an axial flap structure which is contiguous with said transverse edge, said tubular structure having a scalloped portion which opens from said transverse edge, said scalloped portion being contained within said flap structure, said endovascular graft further comprising a stent structure which is connected to said flap structure.

13. An endovascular graft according to claim 12, wherein said flap structure has an inner surface to which said stent structure is connected, said stent structure having a first end and a second end, said stent structure being positioned axially relative to said tubular structure such that said transverse edge is between said first end and said second end of said stent structure.

14. An endovascular graft according to claim 1 comprising:
an attachment member;
wherein said attachment member is positioned on or adjacent to the sealing ring.

15. An endovascular graft according to claim 14, further comprising a graft extension.

16. An endovascular graft according to claim 15, wherein the graft extension is attached to the attachment member.

17. An endovascular graft according to claim 1, wherein said fenestration is a lateral fenestration portion;
wherein said lateral fenestration portion is positioned adjacent to the sealing ring.

18. An endovascular graft according to claim 17, wherein a graft extension is deployed within the lateral fenestration portion.

19. An endovascular graft according to claim 1, further comprising:
a lateral branch portion;
wherein said lateral branch portion is positioned adjacent to the sealing ring.

20. An endovascular graft according to claim 19, wherein a graft extension is deployed within the lateral branch portion.

* * * * *